(12) United States Patent
Jung et al.

(10) Patent No.: US 9,026,224 B2
(45) Date of Patent: May 5, 2015

(54) COMMUNICATION INTERFACE FOR SENSORY STIMULATION

(76) Inventors: Ranu Jung, Miami Beach, FL (US); Kenneth Horch, Fountain Hills, AZ (US); James J. Abbas, Scottsdale, AZ (US); Stephen Phillips, Gilbert, AZ (US); Bertan Bakkaloglu, Scottsdale, AZ (US); Seung-Jae Kim, Phoenix, AZ (US)

( * ) Notice: Subject to any disclaimer, the term of this patent is extended or adjusted under 35 U.S.C. 154(b) by 143 days.

(21) Appl. No.: 13/264,777

(22) PCT Filed: Apr. 21, 2010

(86) PCT No.: PCT/US2010/031936
§ 371 (c)(1),
(2), (4) Date: Jan. 11, 2012

(87) PCT Pub. No.: WO2010/124021
PCT Pub. Date: Oct. 28, 2010

(65) Prior Publication Data
US 2012/0101595 A1   Apr. 26, 2012

Related U.S. Application Data

(60) Provisional application No. 61/171,426, filed on Apr. 21, 2009.

(51) Int. Cl.
*A61N 1/08*    (2006.01)
*A61F 2/68*    (2006.01)
*A61F 2/76*    (2006.01)
*A61N 1/36*    (2006.01)

(52) U.S. Cl.
CPC .......... *A61F 2/68* (2013.01); *A61F 2002/6827* (2013.01); *A61F 2002/7615* (2013.01); *A61F 2002/7625* (2013.01); *A61N 1/36014* (2013.01)

(58) Field of Classification Search
USPC .......................................... 607/62
See application file for complete search history.

(56) References Cited

U.S. PATENT DOCUMENTS

| | | |
|---|---|---|
| 4,165,750 A | 8/1979 | Aleev |
| 4,595,010 A | 6/1986 | Radke |
| 7,221,980 B2 | 5/2007 | Kotlik |
| 8,452,394 B2 * | 5/2013 | Burnes et al. ............ 607/5 |
| 2004/0030361 A1 | 2/2004 | Bosco |
| 2007/0032832 A1 * | 2/2007 | Feher ..................... 607/32 |
| 2007/0270929 A1 * | 11/2007 | Jacobus De Villiers ...... 607/149 |
| 2008/0183098 A1 * | 7/2008 | Denison et al. ............ 600/547 |

OTHER PUBLICATIONS

Anani et al., Human ability to discriminate various parameters in afferent electrical nerve stimulation with particular reference to prostheses sensory feedback, Medical and Biological Engineering & Computing, 1977, 15-4, pp. 363-373.

(Continued)

*Primary Examiner* — Christopher D Koharski
*Assistant Examiner* — Natasha Patel
(74) *Attorney, Agent, or Firm* — Saliwanchik, Lloyd & Eisenschenk

(57) ABSTRACT

Techniques, apparatuses, and systems for interfacing multiple sensors with a biological system can include amplifying signals from respective sensors associated with an external device; modulating the amplified signals based on respective different frequency values; and summing the modulated signals to produce an output signal to stimulate a biological system.

12 Claims, 28 Drawing Sheets

(56) References Cited

OTHER PUBLICATIONS

Anani et al., Afferent electrical nerve stimulation: human tracking performance relevant to prosthesis sensory feedback, Medical and Biological Engineering & Computing, 1979, 17-4, pp. 425-434.

Suh, Development of communication interface for sensory stimulation,Thesis—Arizona State University, May 2009, 54 pages.

Kerkovich, A report on the amputee healthcare and prosthetics workshop sponsored by Walter Reed Army Medical Center and the Department of Veterans Affairs (VA), Guest Editorial, The Journal of Rehabilitation Research & Development (JRRD), May 2004, 41-3B, pp. xiii-xv.

Weir et al., Development of externally-powered prostheses for persons with partial hand amputations, Proceedings of 22nd Annual [IEEE] EMBS International Conference, Jul. 23-28, 2000, 1, pp. 427-430.

Tenore et al., Towards the control of individual fingers of a prosthetic hand using surface EMG signals. Proceeds of the Conference of IEEE Engineering in Medicine & Biology Society (EMBS), Aug. 23-26, 2007, pp. 6145-6148.

Dillingham et al., Limb amputation and limb deficiency: epidemiology and recent trends in the United States, Southern Medical Journal, Aug. 2002, 95-8, pp. 875-883.

Wright et al., Prosthetic usage in major upper extremity amputations, the Journal of Hand Surgery, Jul. 1995. 20A-4, pp. 619-622.

Dhillon et al., Residual function in peripheral nerve stumps of amputees: implications for neural control of artificial limbs, the Journal of Hand Surgery, 2004, 29A-4, pp. 605-615.

Jacobsen et al., Development of the Utah artificial arm, Apr. 1982. IEEE Transactions of Biomedical Engineering, Apr. 1982, BME29-4, pp. 249-269.

Aghili et al., Use of a pattern recognition technique to control a multifunctional prosthesis, Medical and Biological Engineering & Computing, May 1995, 33, pp. 504-508.

Rohland, Sensory feedback for powered limb prostheses, Medical and Biological Engineering, Mar. 1975, 13, pp. 300-301.

Dhillon et al., Effects of short-term training on sensory and motor function in severed nerves of long-term human amputees, J Neurophysiol, May 2005, 93, pp. 2625-2633.

O'Riain et al., Position proprioception in a microcomputer controlled prosthesis, Medical and Biological Engineering & Computing, May 1987, 25, pp. 294-298.

Dhillon et al., Direct neural sensory feedback and control of a prosthetic arm, IEEE Transactions on Neural Systems Rehabilitation Engineering, Dec. 2005, 13-4, pp. 468-472.

CWE Instruments for Physiology and Respiration Data Sheets, FNS-16 Neuromuscular Stimulator, http://www.cwe-inc.com/images/FNS-16%20Stimulator.pdf, Oct. 2004, 2 pages.

Karki, Active Low-Pass Filter Design, 2002, Texas Instruments, Application Report—SLOA049B, Sep. 2002, 24 pages.

International Search Report and Written Opinion of International Application No. PCT/US2010/031936, mailed Dec. 22, 2010, 11 pages.

\* cited by examiner

Signal 1
(440 Hz)

Signal 2
(1610 Hz)

Signal 3
(6740 Hz)

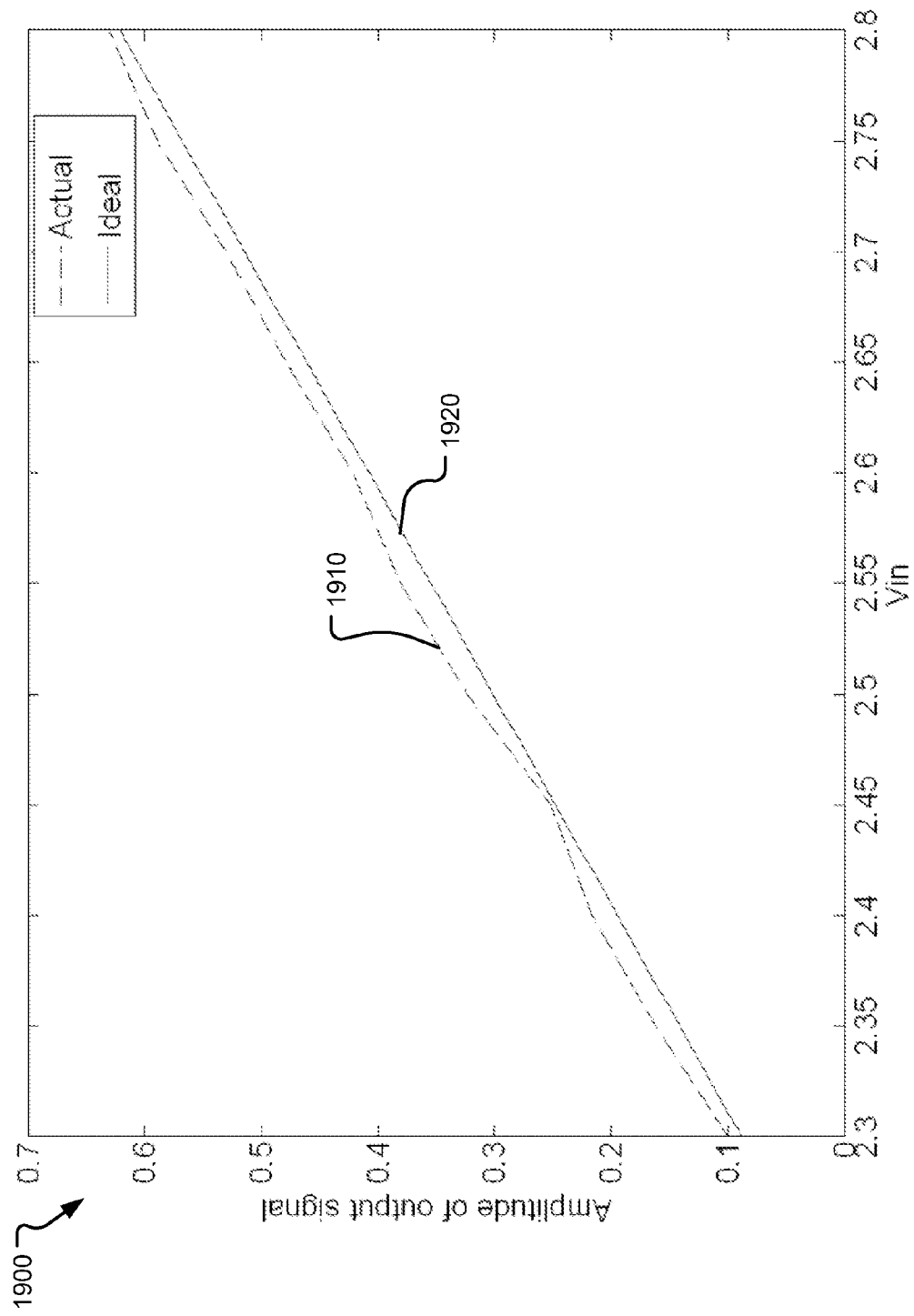

COMMUNICATION INTERFACE FOR SENSORY STIMULATION

CLAIM OF PRIORITY

This application claims priority under 35 USC §119(e) to U.S. patent application Ser. No. 61/171,426, filed on Apr. 21, 2009, the entire contents of which are hereby incorporated by reference.

FEDERALLY SPONSORED RESEARCH OR DEVELOPMENT

The invention was made with government support under Grant No. R01-EB008578 awarded by the National Institutes of Health (NIH). The U.S. Government has certain rights in the invention.

BACKGROUND

This application relates to providing sensory feedback from prosthesis and other fabricated technologies to biological systems via stimulation of biological tissue.

Amputees can use prosthesis such as an artificial limb to regain partial functionality. For example, a person whose arm was amputated can use an artificial arm that replaces some of the functionality of the lost arm. In a different example, a person whose legs were severed can use a pair of prosthetic legs to walk again. Various techniques are available to provide sensory information feedback to prosthetic users. For example, a mechanical, electrical, magnetic, optical or chemical stimulus can be provided to the skin in response to signals derived from external sensors such as a goniometer mounted on the prosthesis. While some individual sensor information can be provided, the capability of communicating information from multiple hardware fabricated sensors and multiple modes of sensation such as force and positioning information simultaneously in a satisfactory manner is lacking.

SUMMARY

This patent application discloses techniques, apparatuses, and systems for interfacing multiple sensors with a biological system via stimulation of biological tissue (for example nerve, skin etc.) to evoke sensation.

In one aspect, techniques, apparatuses, and systems for interfacing multiple sensors with a biological system can include amplifying signals from respective sensors associated with prosthesis or other external devices; modulating the amplified signals based on respective different frequency values; and summing the modulated signals to produce an output signal to stimulate the biological system.

Implementations can include one or more of the following features. Features can include using the output signal to stimulate one or more sites in and on the biological system. Modulating the amplified signals can include varying an amplitude of a reference signal based on one of the amplified signals. Features can include operating digital processing circuitry to receive signals from respective sensors; and operating the digital processing circuitry to produce the output signal to stimulate the biological system.

In another aspect, techniques, apparatuses, and systems can include amplifiers configured to amplify respective sensor signals; modulators configured to modulate respective amplified signals; a summer configured to combine outputs of the modulators to produce an output signal. Each modulator can be configured to use a different frequency for modulation.

Implementations can include one or more of the following features. Implementations can include one or more amplifiers coupled between respective modulators and the summer to effect a weighting of modulator output in the summer. Amplifiers can include a programmable gain amplifier. Implementations can include low pass filters coupled between respective modulators and the summer to remove high frequency components. In some implementations, each modulator can be configured to produce a signal whose amplitude is based on one of the amplified signals. In some implementations, a summer can be configured to use weight values to control a contribution of respective modulator outputs to the output signal.

In yet another aspect, apparatuses and systems for interfacing multiple sensors with a biological system can include multiple sensors and a communication interface in communication with the sensors. The communication interface can perform operations such as amplifying signals from respective sensors; modulating the amplified signals based on respective different frequency values; and summing the modulated signals to produce an output signal to stimulate a biological system.

Implementations can include one or more of the following features. In some implementations, a communication interface can include digital processing circuitry to perform operations. In some implementations, a communication interface can include amplifiers configured to amplify respective sensor signals; modulators configured to modulate respective amplified signals, wherein each modulators is configured to use a different frequency for modulation; and a summer configured to combine outputs of the modulators to produce the output signal. In some implementations, a system can be configured to provide the output to a biological system via one or more electrodes. In some implementations, a system can include a prosthesis that includes the sensors and the communication interface.

The techniques, apparatus and systems described herein can potentially provide one or more of the following advantages. For example, these techniques, apparatus and systems described herein can potentially provide the biological system amputee with improved quality of sensation and control over their prosthetic or other external devices. Similarly, peripheral nerves innervating one muscle and skin region of the amputated limb may be re-routed to target another muscle and skin region. This targeted reinnervation can allow a new area of biological tissue to receive sensory information. By coupling techniques of targeted reinnervation and skin stimulation with better and increased natural sensory feedback, prosthetic devices can be developed to improve their performance and also enable them to be more felt like a part of actual body. In addition, the described techniques, apparatus and systems can be applied to external devices other than prosthetic, such as external devices used by able-bodied persons for performing a task, including robotic arms, scissors or probe tips used by surgeons in non-invasive surgery. Additional applications can include fighter pilots to help them operate the fighter plane and teleoperators operate machines at a distance. Teleoperation indicates operation of a machine at a distance. Teleoperation can include remote control of robotics and mobile robots other environment in which a device or machine is operated by a person from a distance.

These and other aspects and technical features associated with techniques, apparatus, and systems for interfacing multiple sensors with a biological system are set forth in the accompanying drawings, the description, and the claims.

BRIEF DESCRIPTION OF DRAWINGS

FIG. 19 is a data graph showing an output of merged signal.

Like reference numbers represent like features throughout the figures.

DETAILED DESCRIPTION

Figure 1:
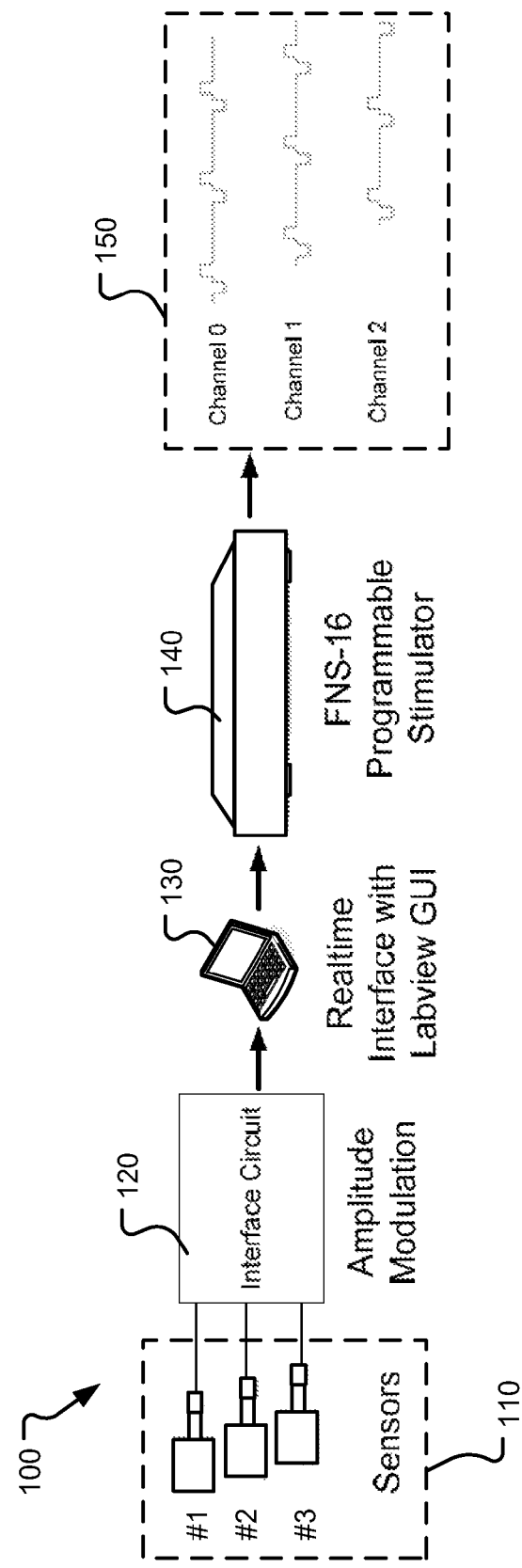
FIG. 1 is a block diagram showing an exemplary sensory-enabled prosthetic system that includes a communication interface for providing sensory information.

Techniques, apparatus and systems are described for implementing a communication interface between fabricated sensors for different modalities such as touch, force, pressure, temperature that are in the prosthesis or other external device and a on-body or in-body stimulator to provide sensory feedback to the biological system. These techniques, apparatus and systems described herein can potentially provide the biological system with improved quality of sensation and control over their prosthetic or other external devices. Examples of external devices can include not only prosthetic, but also external devices used by able-bodied persons for performing a task, such as robotic arms, scissors or probe tips used by surgeons in non-invasive surgery.

Amputated peripheral nerves retain some sensory and motor function. Also, although a limb is amputated, if the remaining peripheral nerve fibers are electrically stimulated, one may be able to perceive tactile and proprioceptive sensations from the phantom limb. Such peripheral nerve stimulation consistently results in discrete, unitary and graded sensations of touch/pressure as well as joint-position sense. By coupling techniques of peripheral nerve fiber stimulation with better and increased natural sensory feedback, prosthetic devices can be developed to improve their performance and also enable them to be more felt like a part of actual body. Similarly, peripheral nerves innervating one muscle and skin region of the amputated limb may be re-routed to target another muscle and skin region. This targeted reinnervation allows a new area of biological tissue to receive sensory information. By coupling techniques of targeted reinnervation and skin stimulation with better and increased natural sensory feedback, prosthetic devices can be developed to improve their performance and also enable them to be more felt like a part of actual body.

As a part of such sensory-enabled prosthetic systems, a communication interface for sensory information can be developed. To provide sensory feedback to prosthetic users, the prosthetic devices use sensors that can acquire information of reacted forces and positioning of the prosthetic arm, hand, digits, or lower limb. These sensor output signals are communicated with a stimulator system, so that that the stimulator system can deliver appropriate current stimulation patterns (amplitude, frequency, and pulse widths) associated with the sensor outputs to the electrodes implanted into the nerve fibers or via vibratory devices. Accordingly, the number of input and output channels for a stimulator system may be determined by: 1) the number of sensor outputs from the prosthesis or external device, that are communicated with the input channels of the stimulator, and also 2) the number of selective electrodes that are connected to the output channels of the stimulator. As a prosthetic/external device becomes more sophisticated thus providing a richer sensory feedback, larger number of sensors may be used. This may in turn increase the number of channels to communicate with the stimulator system, which may possibly add more complications in designing and developing a stimulator system. In addition, if the stimulator system has been developed as a separate module for a prosthetic/external device system, the communication channels for the stimulator may need to be redesigned or modified whenever the number of sensors increases or decreases.

A communication interface implemented according to the techniques, apparatus and systems described herein can enable a stimulator system to communicate with as many sensor outputs from prosthesis/external device as possible regardless of a limited number of input channels of stimulator. For this purpose, sensor output signals are modulated to wave signals with different carrier frequencies and combined into a wave signal where the intensity of sensor outputs can be associated with alteration of the amplitude of modulated wave signals. In this way, communication interface between prosthetic/external device sensor outputs and stimulator inputs can be simplified and the stimulator system can be fully functional even with very limited number of input channels.

A communication interface can combine multiple sensors output to produce one or more signals to electrically, mechanically, chemically, optically or magnetically or other viable approaches to stimulate biological tissue, e.g., simulate one or more nerves associated with a nervous system. Stimulation of nerves and other biological tissue, e.g., through electrodes, can produce graded, discrete sensations such as sensations of touch or movement. For example, a prosthetic hand can include sensors for touch, force, and temperature. A communication interface, which can be located in the prosthesis, can convert the sensor output into a signal to control stimulation of a user's remaining nerves in the arm via one or more electrodes which can be implanted within individual fascicles of peripheral nerve stumps in an amputee. A prosthetic/external device system including sensors and a communication interface can include an on-body or in-body stimulator to provide sensory feedback to the amputee (or biological system). An output of a communication interface can control the stimulator.

Communication Interface Overview

Described herein is a communication interface circuit capable of connecting sensor outputs from an external device with a stimulator. Various aspects of the communication interface circuit are described below including: (1) specification of the communication interface circuit; (2) design of the communication interface circuit; and (3) test results of the communication interface circuit.

Communication Interface System

FIG. 1 is a block diagram showing an exemplary sensory-enabled prosthetic system 100 that includes a communication interface for providing sensory information. Output signals from sensors 110 of a prosthesis or a prosthetic device are provided as input to a communication interface circuit 120. The communication interface circuit 120 can optionally communication with a platform or development environment 130 for data acquisition, instrument control, test automation, analysis and signal processing, industrial control, and embedded design. One example of a development environment is LabVIEW (from National Instruments) graphic user interface (GUI). The development platform 130 can interface with a programmable stimulator or waveform generator 140 (e.g., FNS-16 from CWE Inc.). The programmable stimulator 140 can generate stimulus input signals 150 based on the information received from the communication interface circuit 120 (in some instances through the development environment). Table 1 below shows an example list of frequency and channel allocation for each sensor.

TABLE 1

Frequency to Channel Allocation

| Sensors | Carrier Frequency [Hz] | Allocated Channel |
|---|---|---|
| #1 (0~5 V) | 440 | 0 |
| #2 (0~5 V) | 1610 | 1 |
| #3 (0~5 V) | 6740 | 2 |

Input & Output Characterization of Communication Interface

The input to a communication interface circuit (e.g., communication interface circuit 120) can include a set of time varying voltages that represent the output of the various sensors (e.g., sensors 110) in a prosthetic device. The specifications of the communication interface circuit can take into account the range and frequencies of these voltages. The sensor output ranges are determined before designing the communication interface circuit. This determination of the sensor output ranges can be accomplished, for example, from published manufacturer's data for the sensor and functional characterization of the sensor output over the range of performance of the prosthetic device.

The output characterization of the communication interface circuit can be performed by modeling the sensor output signals. For example, voltage waveforms mimicking the sensor outputs can be generated using a waveform generator. The output of the communication interface circuit can be analyzed responsive to the generated voltage waveforms using time and frequency signal analyses, for example, to document whether the desired signal manipulation has been achieved.

Figure 2:
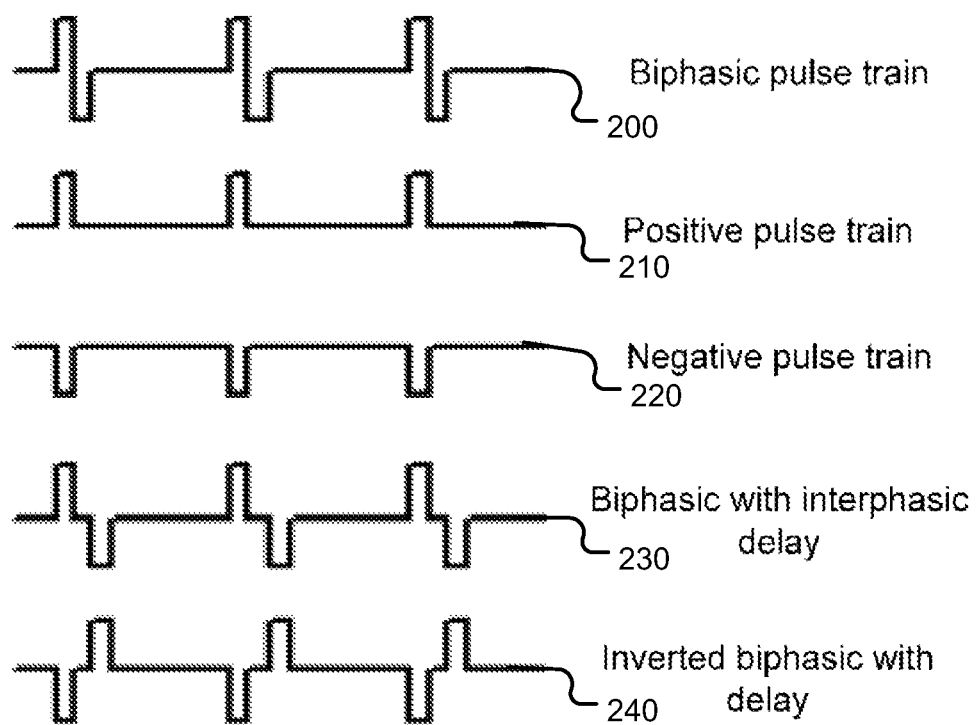
FIG. 2 shows examples of stimulus waveforms that can be used as an input to a communication interface circuit.

Example of Waveforms:

A programmable stimulator or waveform generator (e.g. programmable stimulator 140), such as the FNS-16 stimulator (from CWE, Inc.) can be used to create several fully programmable, constant-current waveforms. Various waveform characteristics, including the timing, polarity, and current amplitude parameters can be modified by a user to generate various waveforms. For example, single pulses can be generated or pulse trains of n pulses, or continuous pulses until a "stop" command is given. The programmable stimulator can be configured to have different number of channels. For example, the programmable stimulator can include 16 independent channels for generating the waveforms. Additional blocks of channels (e.g., sixteen channels) can be added, up to a maximum number of channels (e.g., 256 channels). All outputs of the programmable stimulator can be electrically isolated for low noise and to prevent interference with adjacent recordings. FIG. 2 shows exemplary waveforms 200, 210, 220, 230 and 240 that can be generated by the programmable stimulator. The waveform examples can include: a biphasic pulse train 200, a positive pulse train 210, a negative pulse train 220, a biphasic train with an interphasic delay 230 and an inverted biphasic train with a delay.

Table 1 below shows an example list of specifications of the communication interface circuit.

TABLE 2

Specifications of the interface circuit
Specifications

| | |
|---|---|
| Input Voltage Range | 0~5 V |
| Output Voltage Range | ±supply |
| Output Frequency Range | 20~20 KHz |
| Supply voltage | 5 V |
| Input impedance | High |
| Output impedance | Low |

The above specifications are but one embodiment of the sensor signals. The communication interface can be modified to handle other ranges.

Communication Interface Implementation

The communication interface circuit 120 can be implemented based on the specifications described above. The design for the communication interface circuit 120 can verified using software simulation, such as Simulation Program with Integrated Circuit Emphasis (SPICE) before building the communication interface circuit 120, for example on a breadboard.

Figure 3:
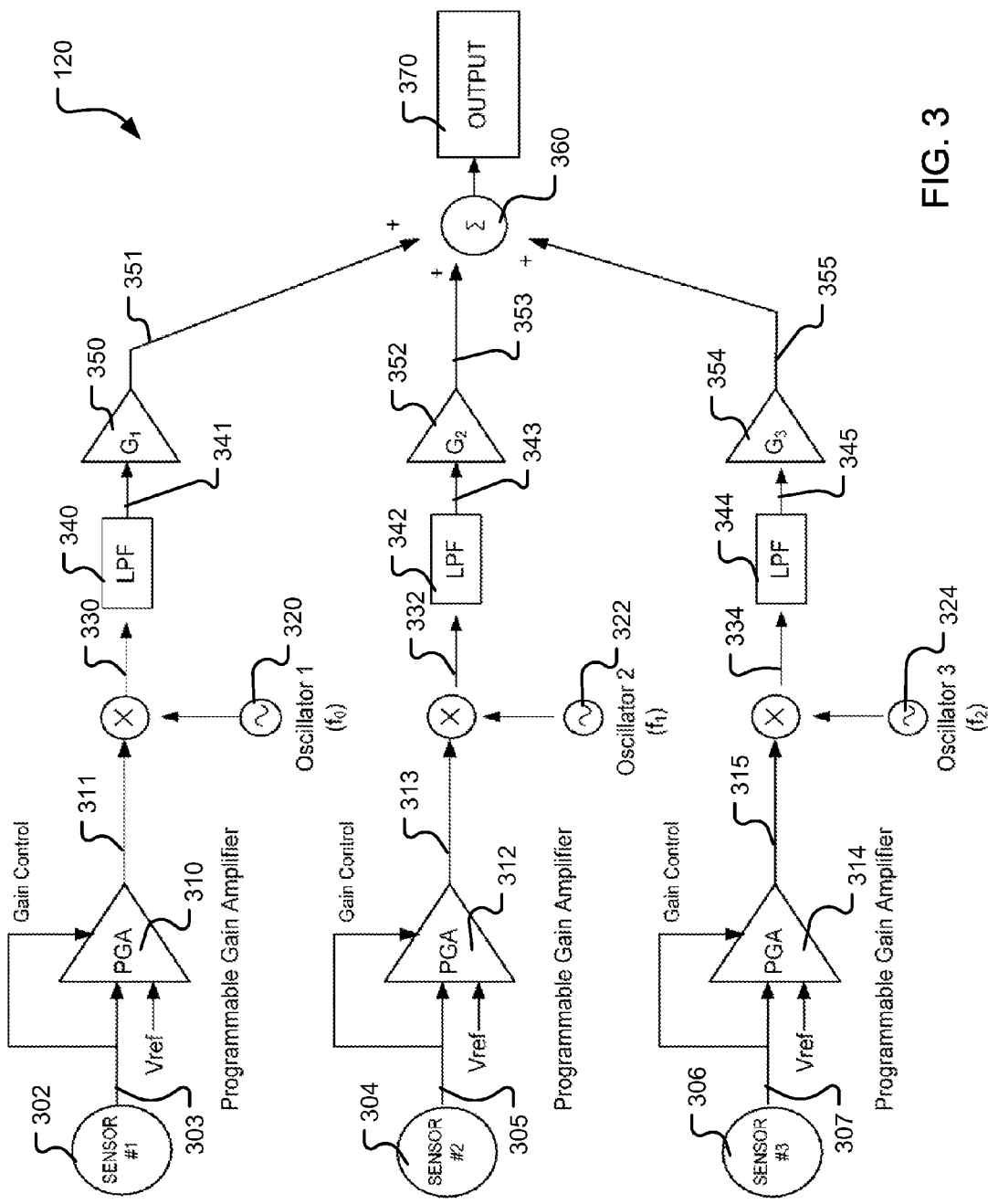
FIG. 3 is a system block diagram showing an exemplary interface circuit.

FIG. 3 shows a block diagram of a communication interface circuit. The communication interface circuit 120 can include amplifiers to amplify respective incoming sensor outputs, respective modulators to modulate the amplified signals, and a summer to combine the modulated signals. In some implementations, a modulator can perform amplitude modulation. Amplitude modulation can dynamically change the amplitude of a signal, such as a signal produced by a frequency oscillator, based on an incoming signal such as an amplified sensor signal.

In some implementations, a communication interface can include multiple programmable gain amplifiers, multiple low frequency sinusoidal oscillators, multiple low pass filters, and a combiner such as a weighted summer. Additionally, a communication interface can include digital processing circuitry, e.g., a processor, specialized logic, and/or digital signal processor, to digitally process sensor data. For example, a processor can be configured to perform the functions of one or more amplifiers, modulators, and summers.

Inputs (e.g., DC voltages) to the communication interface circuit 20 are modulated in each carrier with amplitude variation. For example, a type of Amplitude Modulation (AM), which is common in Radio Frequency (RF) communication, can be implemented. The communication interface circuit can include the following sub-components: Programmable Gain Amplifiers (PGA) 310, 312 and 314; Low Frequency Oscillators (LFOs) 320, 322 and 324; Low Pass Filters (LFPs) 340, 342 and 344; and a Weighted Summer 360.

Design of the Communication Interface Circuit

Outputs 303, 305 and 307 from the sensors 302, 304 and 306 of the prosthesis are amplified by corresponding programmable gain amplifier 310, 312 and 314. The amplified signals 311, 313 and 315 are modulated with signals generated by corresponding low frequency oscillators 320, 322 and 324. The LPFs 340, 342 and 344 degrade the high frequency harmonics of the modulated signals 330, 332, and 334. Examples of LPFs can include second order LPFs. The filtered signals 341, 343 and 345 are amplified using op-amps 350, 352 and 354 having gains G1, G2 and G3 respectively. The amplified signals 351, 353 and 355 are merged together using the Weighted Summer 360 to generate an output signal 370. While FIG. 3 shows the communication interface circuit receiving output signals from three sensors, the total number of sensors can vary to include more or less than the three shown. The number of the sensors can depend on the prosthesis, for example.

Figure 4:
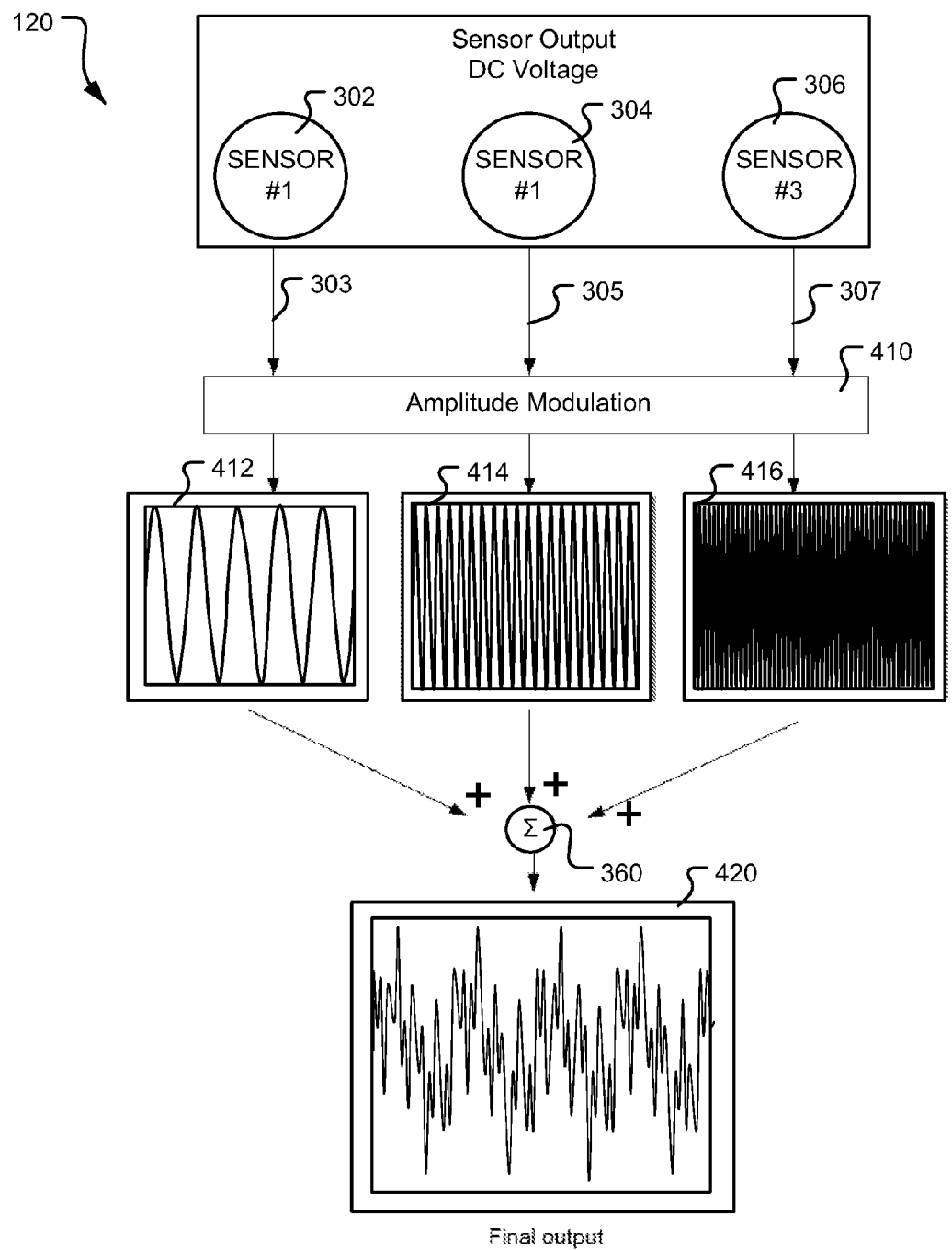
FIG. 4 is a block diagram showing an exemplary output signal of an interface circuit.

FIG. 4 is a block diagram showing an output signal of the communication interface circuit 120. For illustrative purposes, three sensors 302, 304 and 306 are shown. However, as described above, the communication interface circuit 120 can be configured to interface with different number of sensors. The DC voltage sensor output signals 303, 305 and 307 from the sensors 302, 304 and 306 are amplified using an amplitude modulation unit 410. The amplitude modulated signals 412, 414 and 416 are merged using a weighted summer 360 to obtain an output signal 420. The amplitude modulated signals 412, 414 and 416 can be substantially similar to signals 311, 313 and 315 or signals 351, 353 and 355 depending on the circuit sub-components included in the communication interface circuit 120. Also, the output signal 420 can be substantially similar to the output signal 370.

Programmable Gain Amplifier

Figure 5:
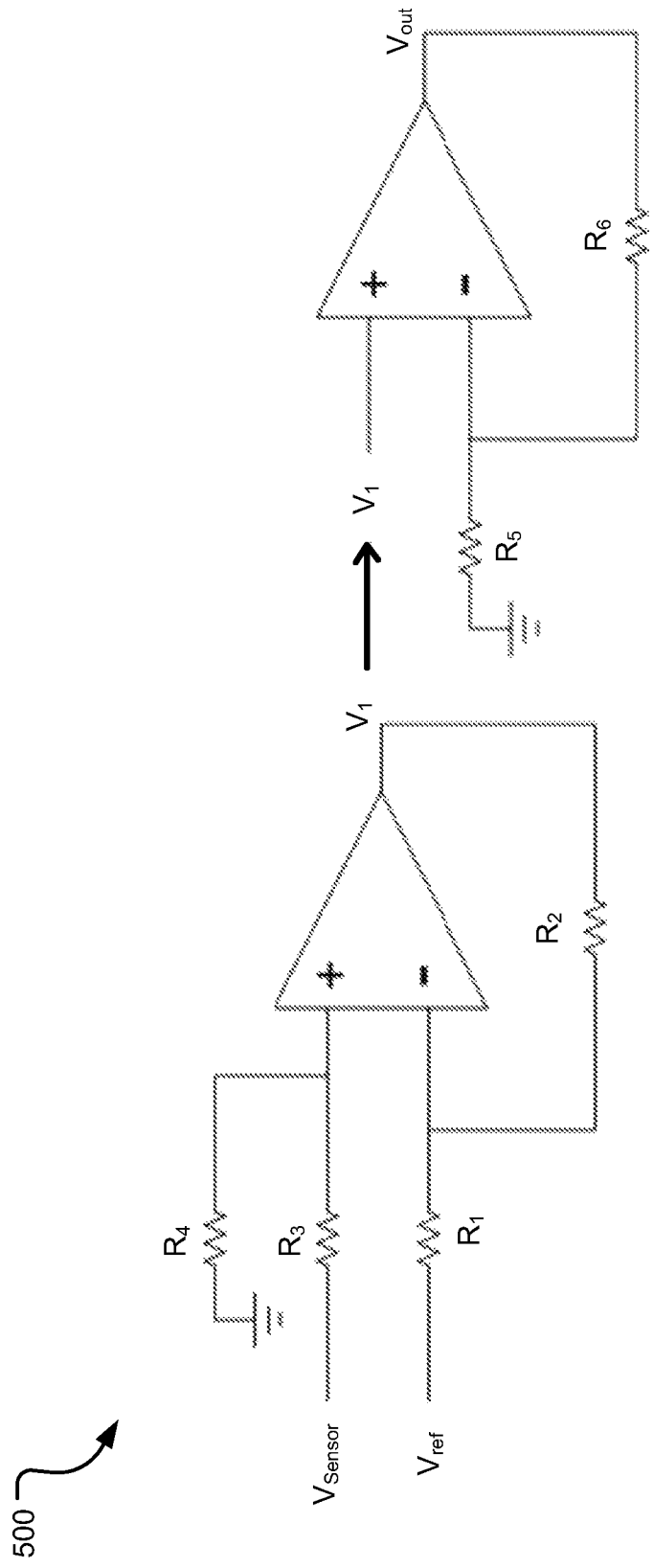
FIG. 5 is a circuit diagram showing a Programmable Gain Amplifier (PGA).

FIG. 5 shows a block diagram of an exemplary PGA. The PGA 500 can be substantially similar to the PGS 310, 312 and 314. The PGA 400 can be configured or programmed to have a selectable gain. For example, the PGA can be programmed either for selectable decade gains such as 10, 100, 1000, etc., or for binary gains such as 1, 2, 4, 8, etc. The choice of the gains can be dependent on the desired function of the end system. To obtain a wide dynamic range, a method of adjusting the input signal level is implemented. A high gain is needed for small sensor voltages, but with a large output, a high gain can cause the amplifier to saturate. With this in mind, a predictably controllable gain device can be implemented. Such a gain device can be configured to have a gain that is controlled by a DC voltage. The PGA 400 is an example of such gain device. The PGA's gain can be conveniently changed via a reference voltage ($v_{ref}$) and resistors.

Because the sensor output voltages (DC) are too big to amplify, the sensor output is lowered by subtracting a certain voltage ($V_{ref}$).

If $R_1=R_2=R_3=R_4$, then $V_1 = V_{SENSOR} - V_{ref}$ (1)

Then $$V_{out} = \left(1 + \frac{R_6}{R_5}\right)V_1.$$ (2)

Therefore the total gain can be determined using $$\frac{V_{out}}{V_{SENSOR}} = \left(1 + \frac{R_6}{R_5}\right) - \left(1 + \frac{R_6}{R_5}\right)\frac{V_{ref}}{V_{SENSOR}}$$ (3)

Figure 6:
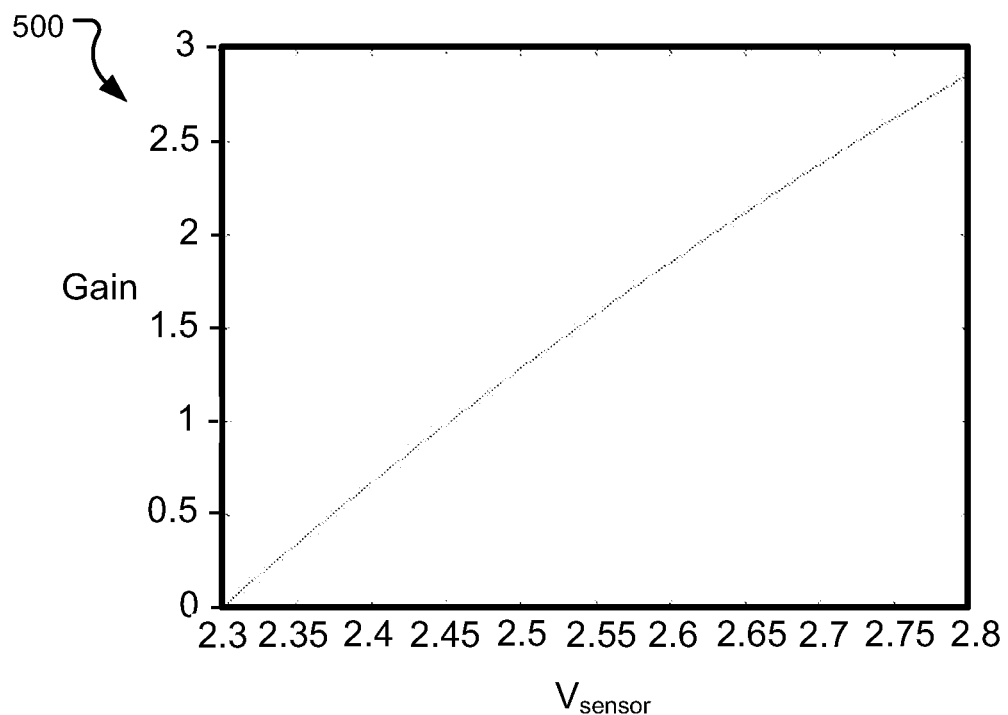
FIG. 6 is a data graph showing a relationship between $V_{sensor}$ and PGA gain.

To make the gain positive, $V_{SENSOR}$ can be modified to be greater than $V_{ref}$. FIG. 6 shows a relationship between the gain and $V_{sensor}$. As the sensor output voltage is increased, the gain can also be increased.

Sinusoidal Oscillator

Figure 7:
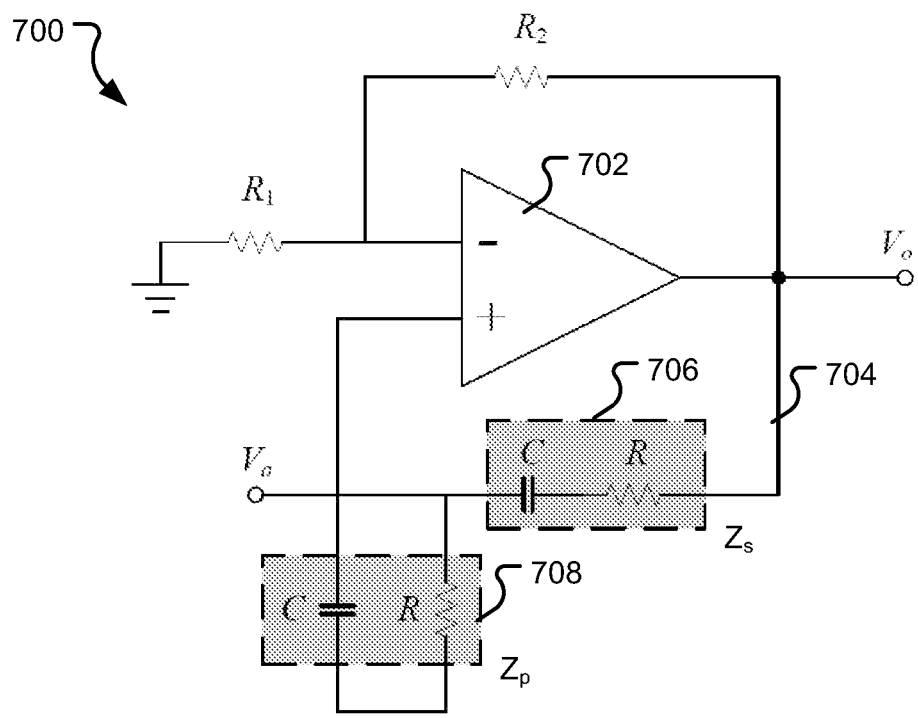
FIG. 7 is a circuit diagram shows a Wien-bridge oscillator.

One of the simplest oscillator circuits is based on the Wien-bridge. The Wien-bridge oscillator is normally based on an amplifier with a positive feedback path build from a series RC circuit and a parallel RC circuit. The oscillators 320, 322 and 324 can be implemented as a Wien-bridge oscillator. FIG. 7 shows a Wien-bridge oscillator 700 without a nonlinear gain-control network. The Wien-bridge oscillator circuit 700 can include or consist of an op amp 702 connected in the non-inverting configuration, with a closed-loop gain of $1+R_2/R_1$.

In a feedback path 704 of the positive-gain amplifier 702, a resistor-capacitor (RC) network (includes $Z_p$ 706 and $Z_s$ 708) is connected. The loop gain can be obtained by multiplying the transfer function $V_a(s)/V_o(s)$ of the feedback network by the amplifier gain, $$L(s) = \left[1 + \frac{R_2}{R_1}\right]\frac{Z_p}{Z_p + Z_s}$$ (4)

Thus, $$L(s) = \frac{1 + \frac{R_2}{R_1}}{3 + sCR + \frac{1}{sCR}}$$ (5)

Substituting s=jw results in $$L(j\omega) = \frac{1 + \frac{R_2}{R_1}}{3 + j\left(\omega CR - \frac{1}{\omega CR}\right)}$$ (6)

The loop gain can be a real number (i.e., the phase will be zero) at one frequency given by $$\omega_0 CR = \frac{1}{\omega_0 CR} \quad (7)$$

That is $$\omega_0 = \frac{1}{CR} \quad (8)$$

Figure 8:
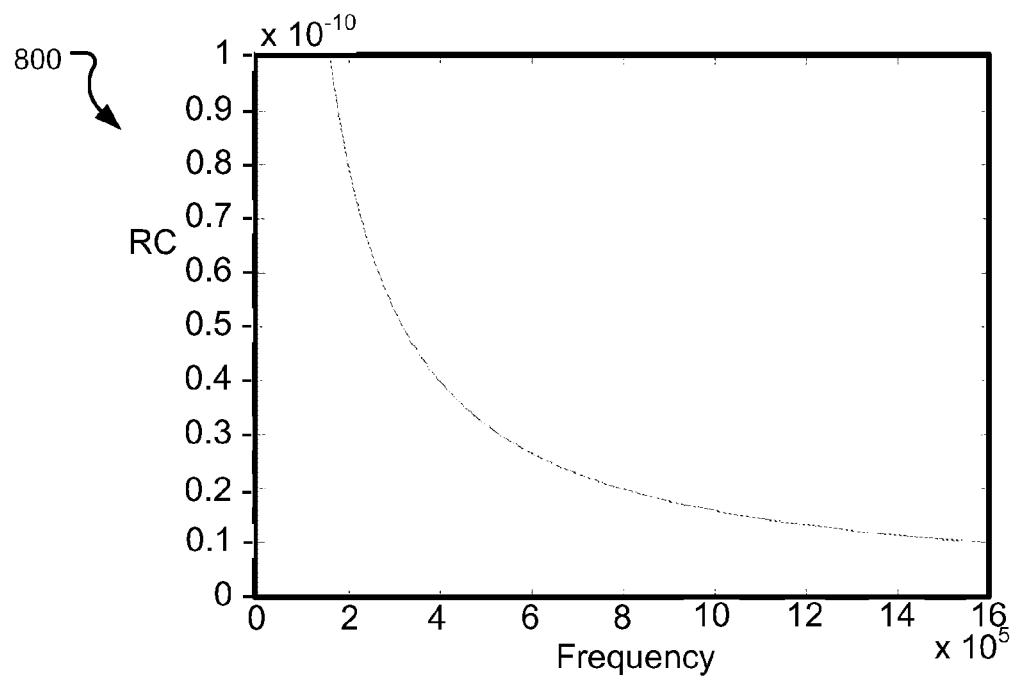
FIG. 8 is a data graph showing a relationship RC versus Frequency.

FIG. 8 is a data chart showing a relationship between RC and frequency. To obtain sustained oscillations at the frequency described above, the magnitude of the loop gain can be set to unity. This can be achieved by selecting $$\frac{R_2}{R_1} = 2 \quad (9)$$

To ensure that oscillations will start, one can choose R2/R1 slightly greater than 2. If $R_2/R_1=2+\delta$, where $\delta$ is a small number, the roots of the characteristic equation $1-L(s)=0$ will be in the right half of the s plane.

Figure 9:
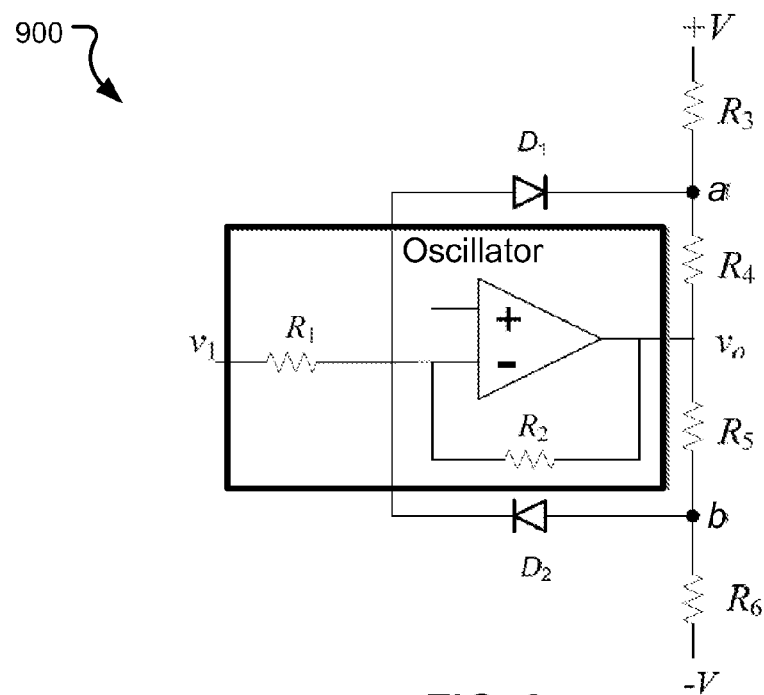
FIG. 9 is a circuit diagram showing a Wien-bridge oscillator with a limiter used for amplitude control.
Figure 10:
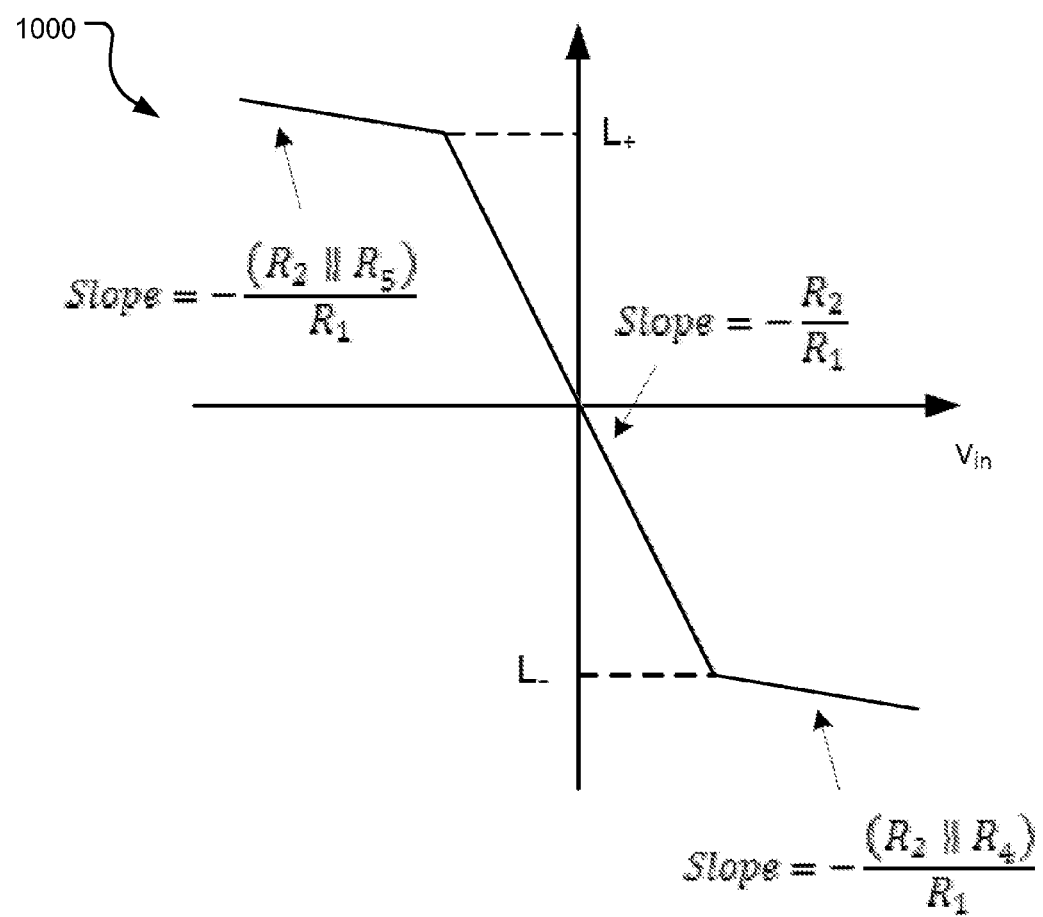
FIG. 10 is a data graph showing amplitude control.

FIG. 8 shows a Wien-bridge oscillator 800 with a limiter used for amplitude control. The amplitude of oscillation can be determined by using a nonlinear control network. FIG. 9 shows controlling the amplitude of oscillation. The amplitude of oscillation can be shaped by diodes $D_1$ and $D_2$ together with resistors $R_3$, $R_4$, $R_5$, and $R_6$. At the positive peak L+ of the output voltage $v_o$, the voltage at node b exceeds the voltage v1 (which is about $$\frac{R_3}{R_4} = v_0),$$

and diode D2 conducts.

This will clamp the positive peak to a value determined by R5, R6, and the negative power supply −V. The value of the positive output peak can be calculated by setting $v_b=v_1+V_{D2}$ and writing a node equation at node b while neglecting the current through D2.

$$L_+ = +V\frac{R_5}{R_6} + V_{D2}\left(1 + \frac{R_5}{R_6}\right) \quad (10)$$

Similarly, the negative peak L− of the output sine wave will be clamped to the value that causes diode D1 to conduct. The value of the negative peak can be determined by setting $v_a=v_1-V_{D2}$ and writing and equation at node a while neglecting the current through D1. To obtain a symmetrical output waveform, R3 is chosen equal to R6, and R4 equal to R5.

$$L_- = -V\frac{R_3}{R_4} + V_{D2}\left(1 + \frac{R_3}{R_4}\right) \quad (11)$$

Figure 11:
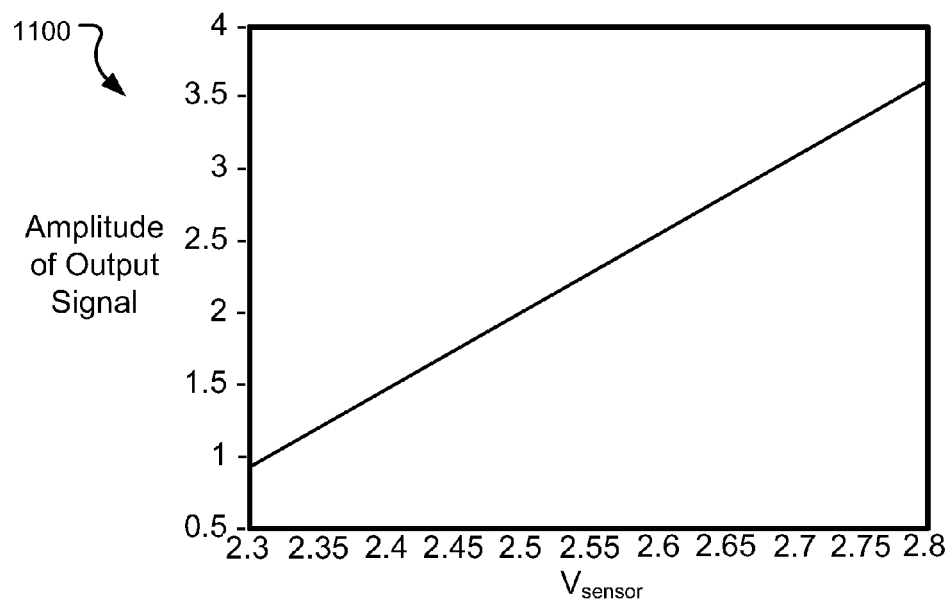
FIG. 11 is a data graph showing a relationship between amplitude of output signal and $V_{sensor}$.

FIG. 11 is a data graph showing a relationship between the amplitude of the output signal and $V_{sensor}$.

Second-Order Low Pass Filter

The transfer function HLP of a second-order low-pass filter can be express as a function of frequency (f).

$$H_{LP}(f) = -\frac{K}{\left(\frac{f}{FSF \times f_c}\right)^2 + f\frac{1}{Q}\frac{f}{FSF \times f_c} + 1} \quad (12)$$

In Equation 2, f is the frequency variable, $f_c$ is the cutoff frequency, FSF is the frequency scaling factor, and Q is the quality factor. There are three regions of operation: below cutoff, in the area of cutoff, and above cutoff.

For each area, Equation 12 can be simplified as follows:

$f \ll f_c \rightarrow H_{LP}(f) \cong K$, the circuit passes signals multiplied by the gain factor K;

$$\frac{f}{f_c} = FSF \rightarrow H_{LP}(f) = -jKQ$$

signals are phase-shifted 90° and modified by the Q factor; and $$f \gg f_c \rightarrow H_{LP}(f) \cong -K\left(\frac{FSF \times f_c}{f}\right)^2$$

signals are phase-shifted 180° and attenuated by the square of the frequency ratio.

With attenuation at frequencies above $f_c$ increasing by a power of 2, the last formula describes a second-order low-pass filter. The frequency scaling factor (FSF) is used to scale the cutoff frequency of the filter so that it follows the definitions given earlier. It is common practice to refer to a circuit as a Butterworth filter or a Bessel filter because its transfer function has the same coefficients as the Butterworth or the Bessel polynomial. It is also common practice to refer to the Multiple Feedback (MFB) or Sallen-Key circuits as filters. The difference is that the Butterworth filter defines a transfer function that can be realized by many different circuit topologies whereas the MFB or Sallen-Key circuits are specific implementation topologies. The choice of circuit topology depends on performance requirements. The MFB is generally preferred because it has better sensitivity to component variations and better high-frequency behavior. The unity-gain Sallen-Key inherently has the best gain accuracy because its gain is not dependent on component values.

Figure 12:
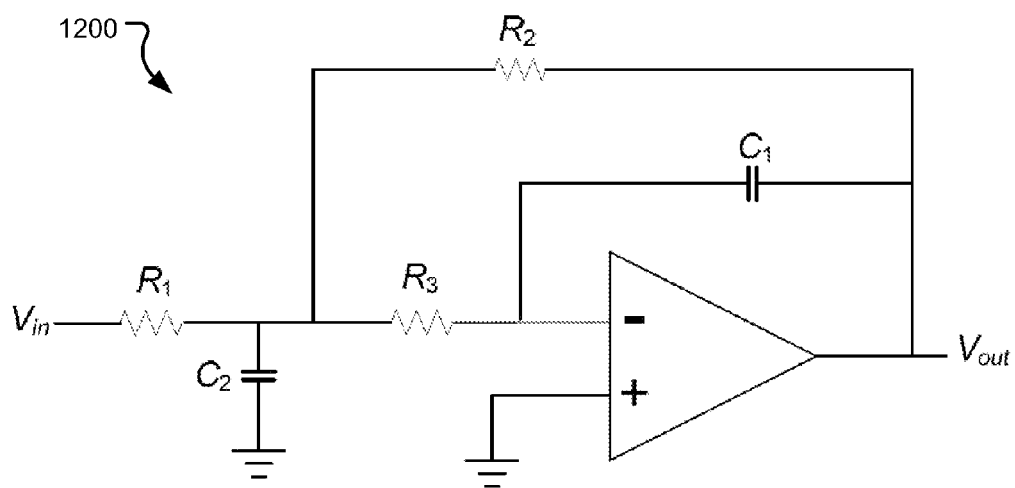
FIG. 12 is a circuit diagram showing a Low-Pass MFB Architecture.

FIG. 12 is a block diagram of a Low-Pass MFB Architecture. FIG. 12 shows the MFB filter architecture and its ideal transfer function.

$$H(f) = \frac{-\frac{R_2}{R_1}}{(j2\pi f)^2(R_2 R_3 C_1 C_2) + j2\pi f\left(R_3 C_1 + R_2 C_1 + \left(\frac{R_2 R_3 R_1}{R_1}\right)\right) + 1} \quad (13)$$

If the following substitutions are made:

$$K = \frac{-R_2}{R_1}, \quad (14)$$

$$FSF \times f_c = \frac{1}{2\pi\sqrt{R_2 R_3 C_1 C_2}},\quad (15)$$

And $$Q = \frac{\sqrt{R_2 R_3 C_1 C_2}}{R_3 C_1 + R_2 C_1 + R_3 C_1(-K)} \quad (16)$$

Then Equation 13 becomes the same as Equation 12. Additionally, the design process could be simple if these simplifications are used.

Letting $R_2=R$, $R_3=mR$, $C_1=C$, $C_2=nC$ and $K=-1$ results in:

$$FSF \times f_c = \frac{1}{2\pi RC\sqrt{mn}} \quad (17)$$

and $$Q = \frac{\sqrt{mn}}{1+m(1-K)} \quad (18)$$

This sets the gain=0 dB in the pass band. Design should start by determining the ratios m and n for the needed Q of the filter, and then selecting C and calculating R to set $f_c$.

Figure 13:
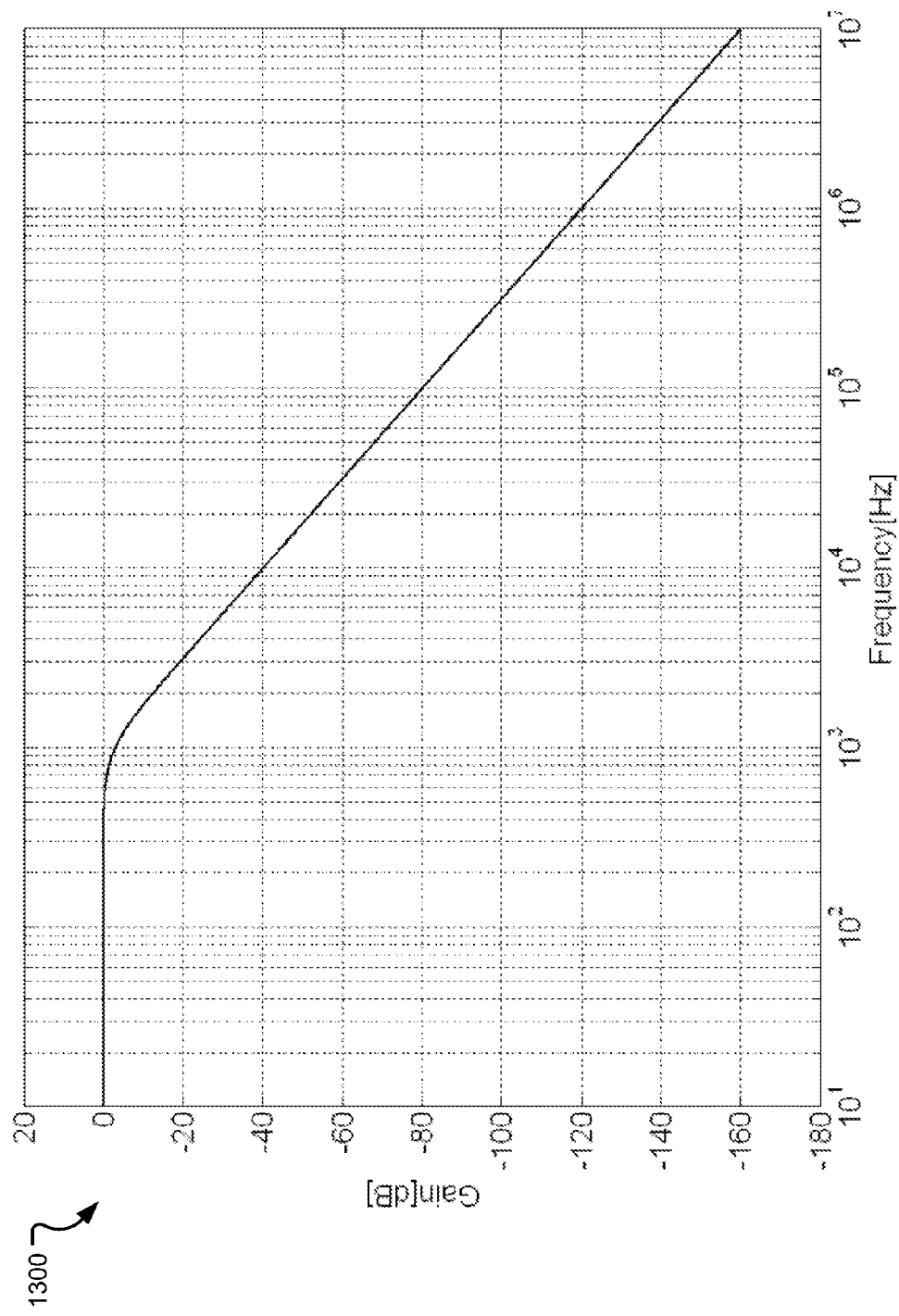
FIG. 13 is a data graph showing a MFB filter frequency response.
Figure 14:
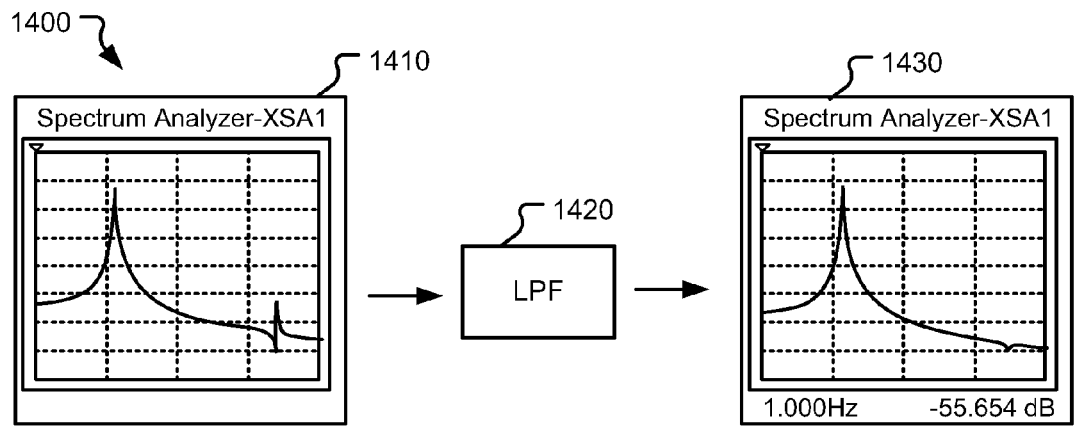
FIG. 14 is a block diagram showing a MFB filter simulation result.

As an example, for a 1 kHz cutoff frequency we may choose. $R_2=R_1=15.5$ kΩ, $R_3=3.48$ kΩ, $C_1=0.01$ μF and C2=0.047 NF. FIG. 13 is a data graph 1300 showing a frequency response of this low pass MFB filter. FIG. 14 is a block diagram showing a simulated result (e.g., using SPICE) of the low pass MFB filter. The signal before filtering 1410 is shown on the left. After the signal 1410 is filtered using the low pass MFB filter 1420, the filtered result 1430 is shown on the right. The low pass filters 340, 342, 344 and 1200 can be implemented using the lows pass MFB filter 1410.

Weighted Summer

Figure 15:
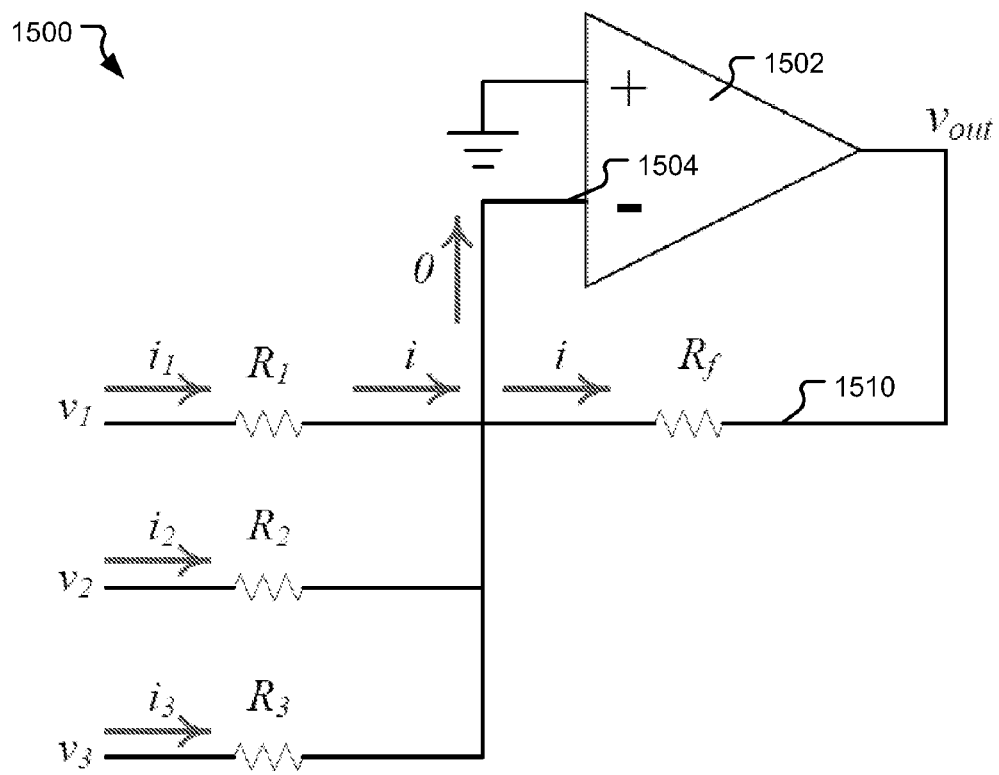
FIG. 15 is a circuit diagram showing a weighted summer.

In the communication interface circuit, the different sensor signals, after processing, are combined with gains applied to the processed sensor signals. A weighted summer can be used to combine the signals. For illustrative purposes, three sensor signals are shown, but the total number of sensors can be varied as described above. Figure An example of a weighted summer circuit 1500 is shown in FIG. 15. The weigh summer 1500 includes a resistance $R_f$ in the negative-feedback path 1510 of an op amp 1502, but there are a number of input signal $v_1$, $v_2$, $v_3$ each applied to a corresponding resistor $R_1$, $R_2$, $R_3$, which are connected to the inverting terminal of the op amp 1502. An ideal op amp has a virtual ground appearing at its negative input terminal 1504. From Ohm's law, the currents $i_1$, $i_2$ and $i_3$ are given by $$i_1 = \frac{v_1}{R_1}, \quad (19)$$

$$i_2 = \frac{v_2}{R_2} \text{ and} \quad (20)$$

$$i_3 = \frac{v_3}{R_3}. \quad (21)$$

All these currents sum together and the current 'i' is produced. Because no current flows into the input terminals of an ideal op amp, the current is forced to flow through $R_f$.

The output voltage $v_{out}$ can be determined by another application of Ohm's law, $$v_{out} = 0 - iR_f = -iR_f \quad (22).$$

Thus, $$v_{out} = -\left(\frac{R_f}{R_1}v_1 + \frac{R_f}{R_2}v_2 + \frac{R_f}{R_3}v_3\right) \quad (23)$$

That is, the output voltage is a weighted sum of the input signals $v_1$, $v_2$, and $v_3$.

Characteristics of the Interface Circuit

Figure 16:
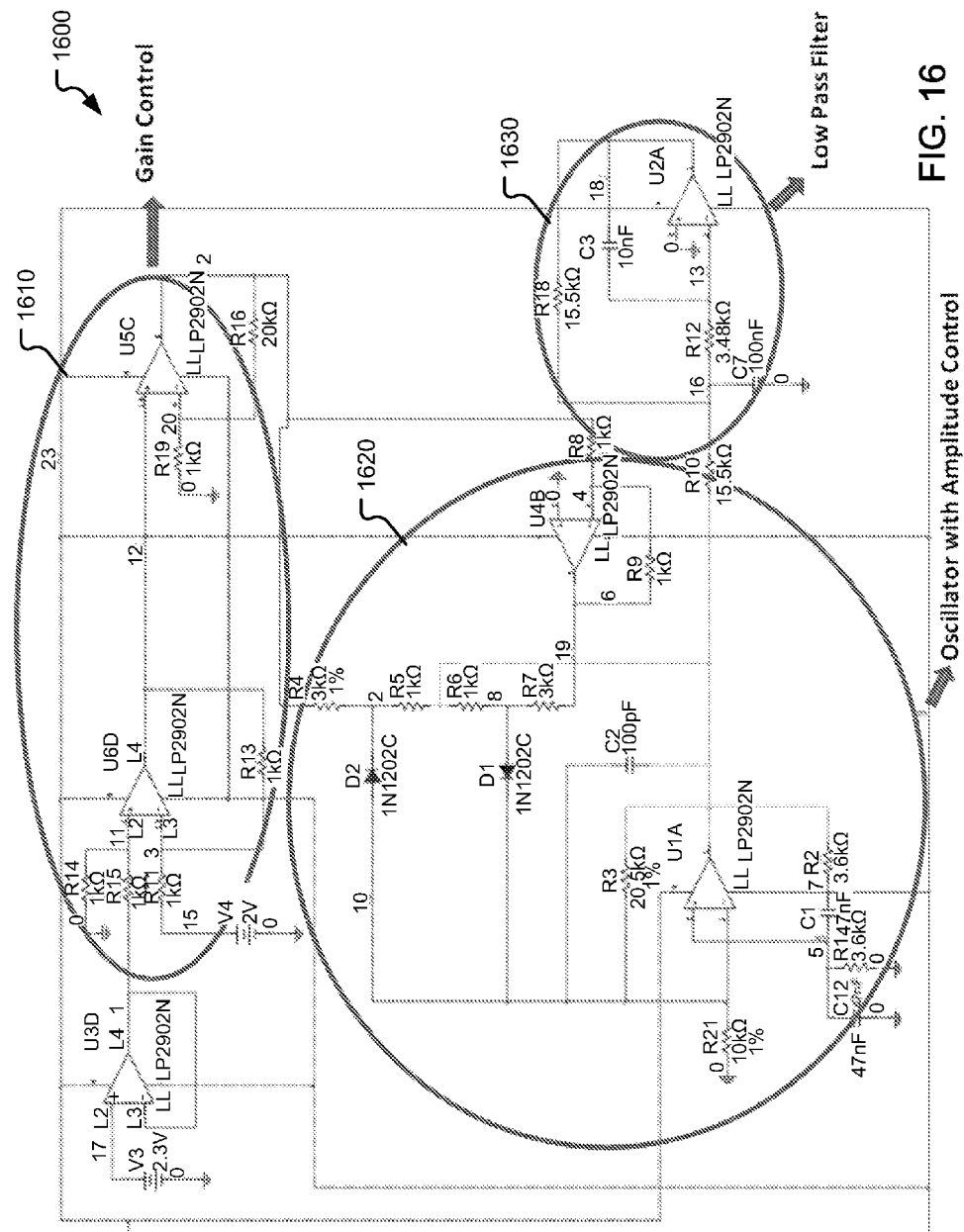
FIG. 16 is a schematic diagram showing an interface circuit.

FIG. 16 shows a schematic diagram 1600 of a communication interface circuit. The communication interface circuit 1600 includes a gain control circuit 1610, an oscillator circuit with amplitude control 1620 and the low pass filter circuit 1630. The gain of sensor output signal can be determined based on $v_{ref}$ and the resistance of the gain control circuit 1630. Additionally, the oscillation frequency can be controlled by adjusting the values of capacitance and resistance used in the oscillator circuit 1620. Simulation results of the communication interface circuit 1600 can be obtained from MultiSim. The communication interface circuit 120 can be implemented similar to the communication interface circuit 1600.

Figure 17A:
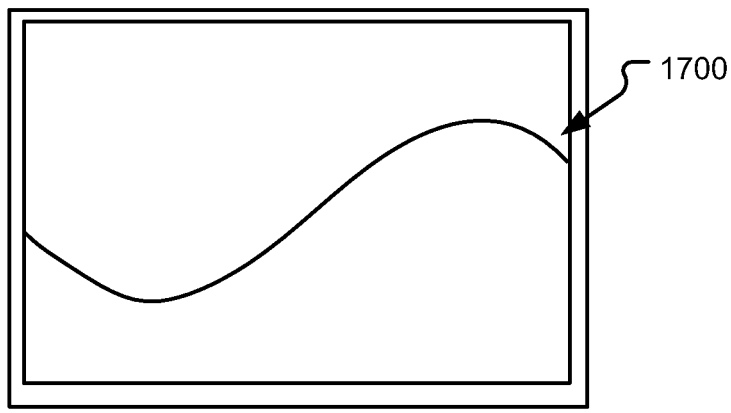
FIGS. 17A, 17B and 17C show a signal output of each sensor.
Figure 17B:
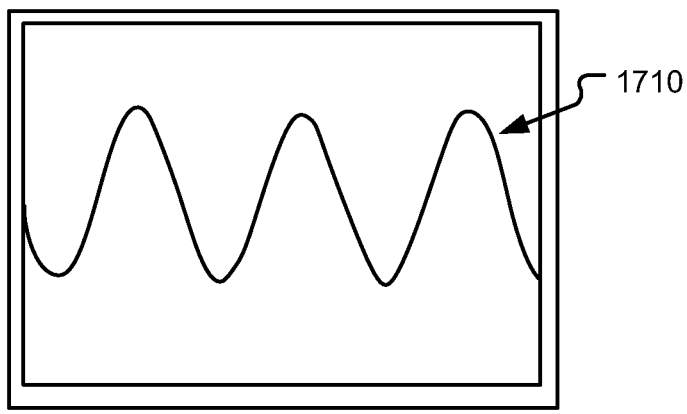
Figure 17C:
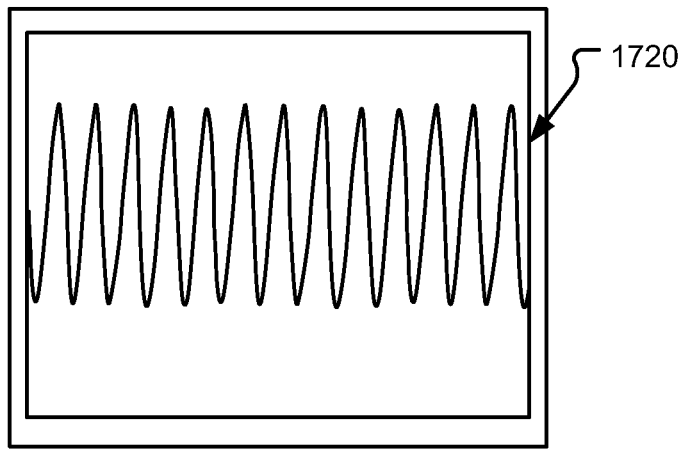

The communication interface circuit 1600 can be built on a Breadboard for testing. FIGS. 17A, 17B and 17C show signals that are modulated from the input signals received from corresponding sensors. For illustrative purposes, three modulated signals 1700, 1710 and 1720 from three sensors are shown. The modulated signals are shown to have different frequencies.

Figure 18A:
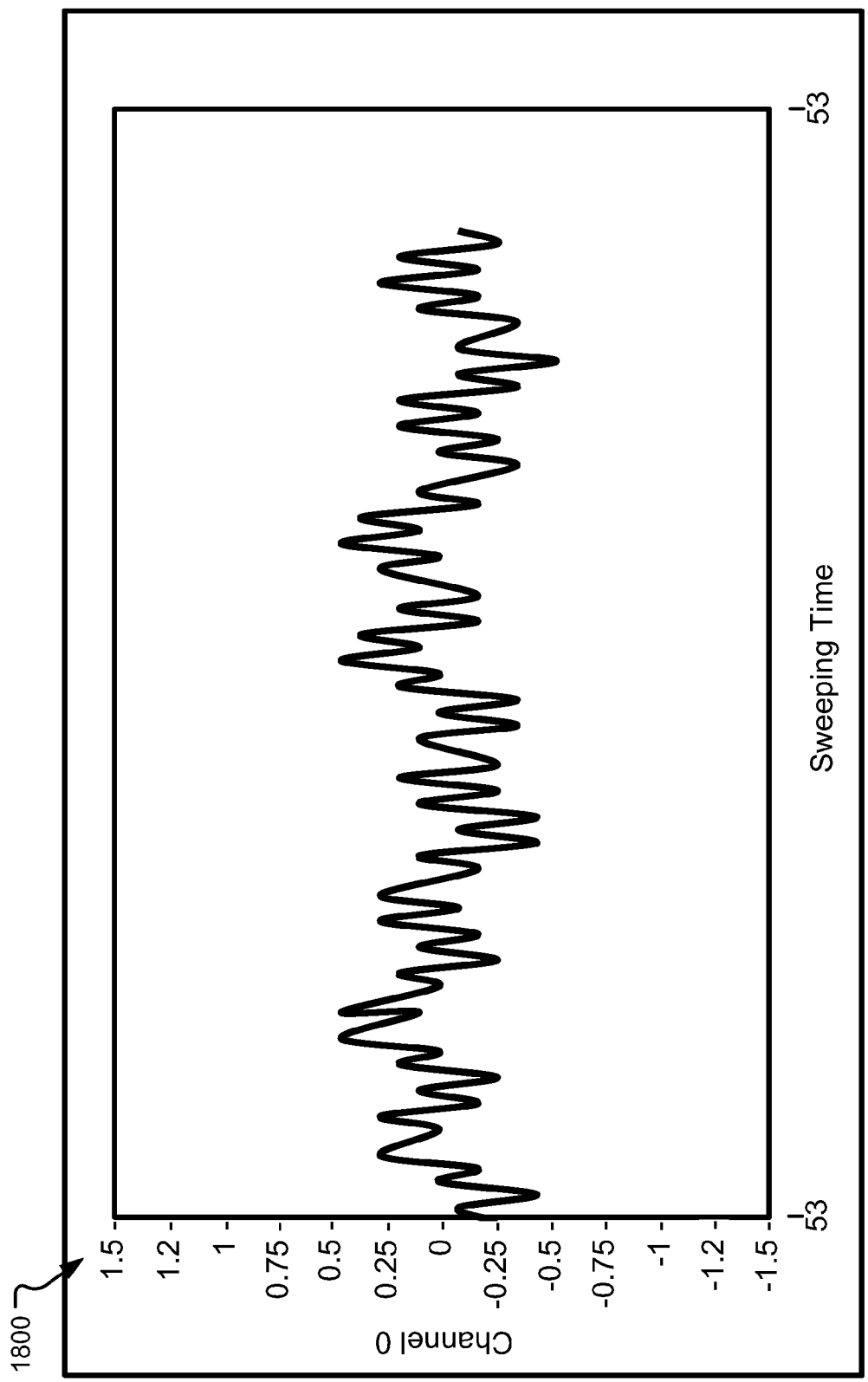
FIGS. 18A and 18B show an output of a merged signal and its spectrum respectively.
Figure 18B:
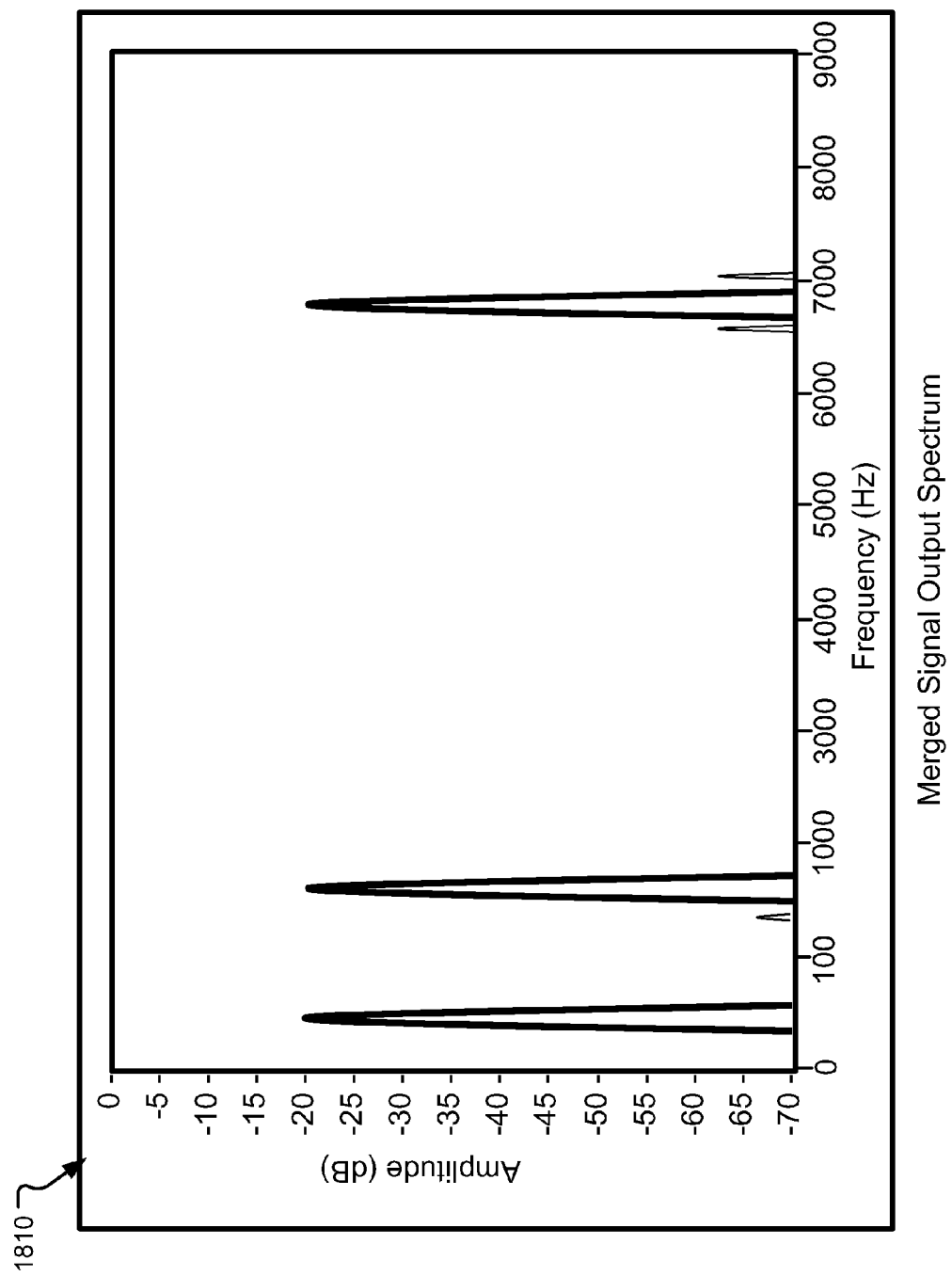

FIG. 18A shows an example of a merged signal 1800 obtained from merging each of three sensor signals. FIG. 18B shows a merged signal output spectrum 1810. FIG. 19 shows output data 1900 of a merged signal comparing the actual output 1910 obtained vs. an ideal output 1920 estimated.

Testing Results

Figure 20:
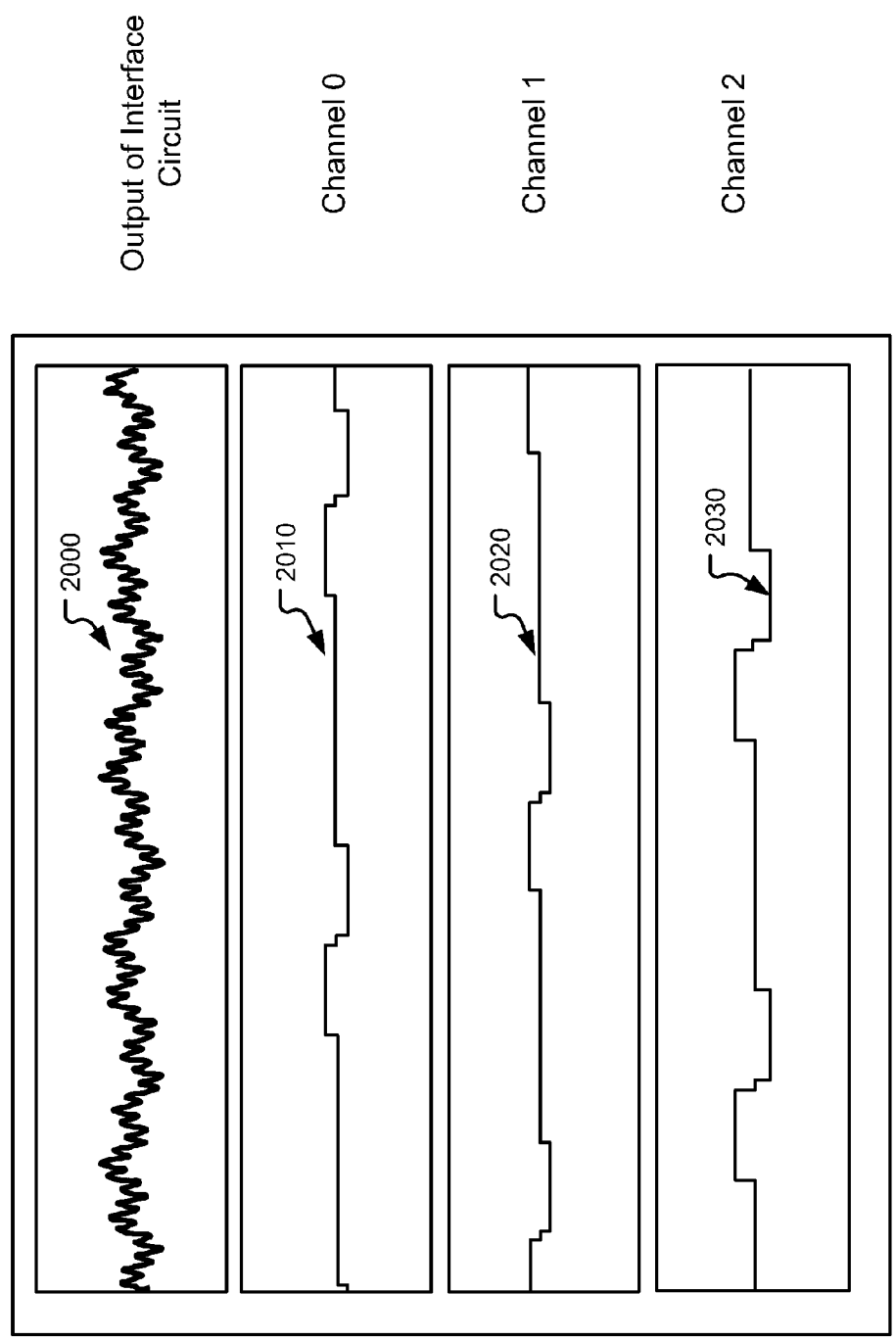
FIG. 20 shows an interface circuit output and digitized stimulus pulses delivered by three channels.

FIG. 20 shows digitized stimulus pulses 2020, 2030 and 2040 delivered by three channels, channel 0, 1 and 2, respectively, as well as an output signal 2010 of a communication interface circuit. For the example shown in FIG. 20, all signals are sampled at a 300 KHz rate. As shown in the FIG. 20, the stimulation patterns are generated sequentially. Therefore, 5 ms after the stimuli comes from channel 0, the next stimulation occurs from channel 1, consecutively, the same process is repeated from channel 2 after 5 ms, for example.

Figure 21A:
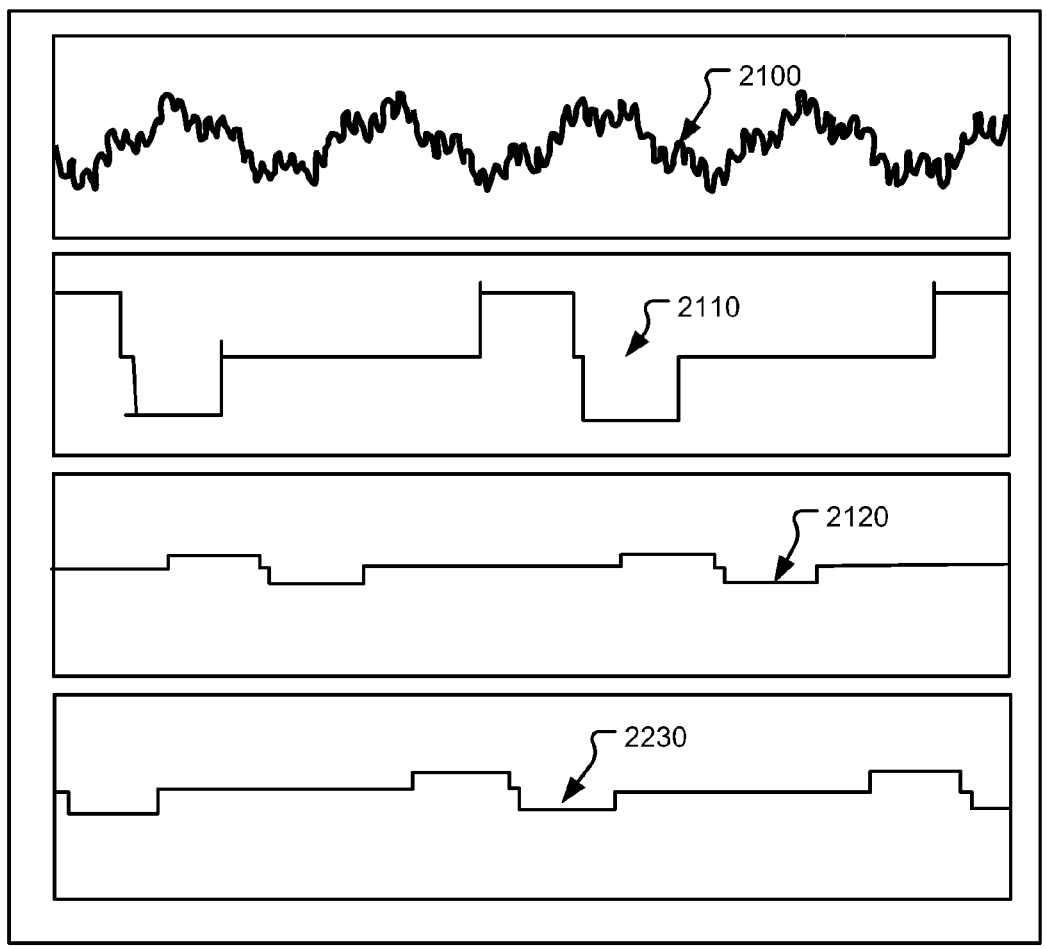
FIGS. 21A and 21B show an output of 3 different channels against the change of sensor #1 input value of 2.5V and 2.8V respectively.
Figure 21B:
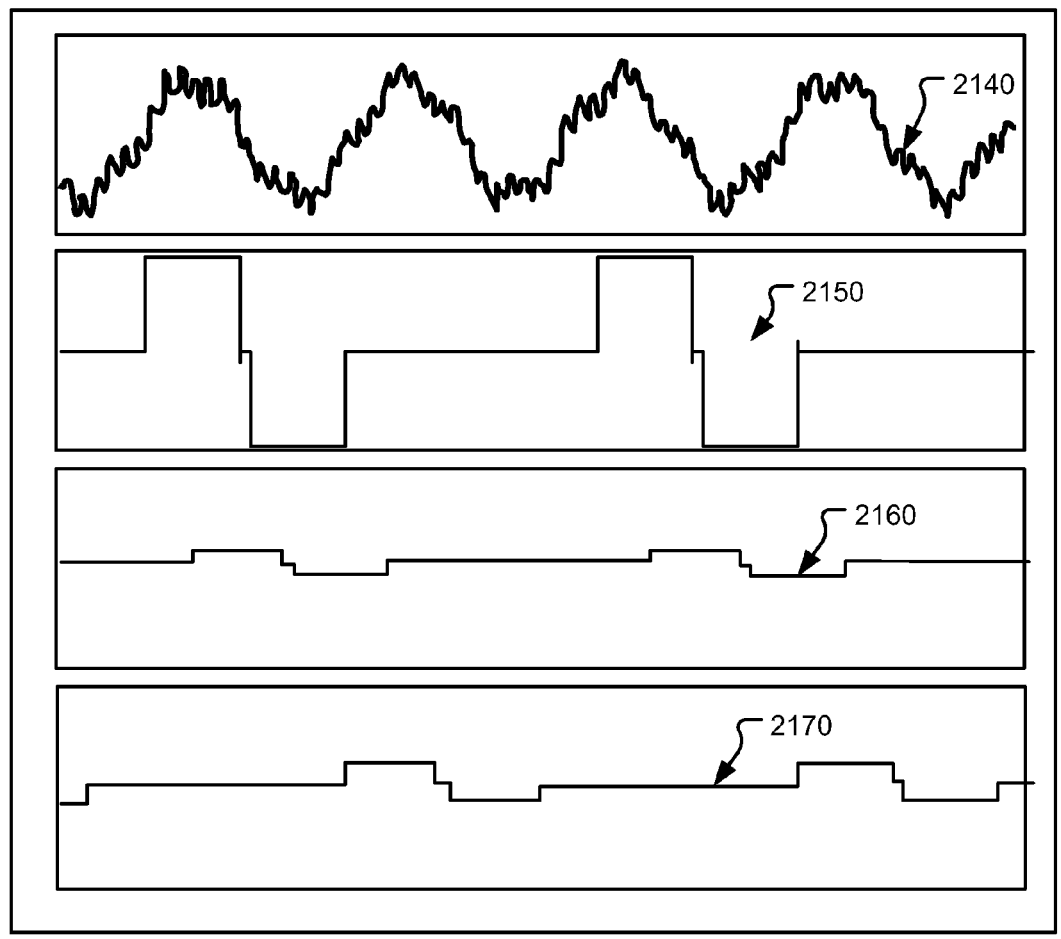

FIGS. 21A and 21B show output signals of different channels (e.g., channels 0, 1 and 2) in response to amplitude change of sensor #1 input value. In FIG. 21A, the output signals 2110, 2120 and 2130 for the different channels are measured after altering the voltage level of sensor #1 (2100) to 2.5V. In FIG. 21B, the output signals 2150, 2160 and 2170 for the different channels are measured after altering the voltage level of sensor #1 (2140) to 2.8V.

Figure 22A:
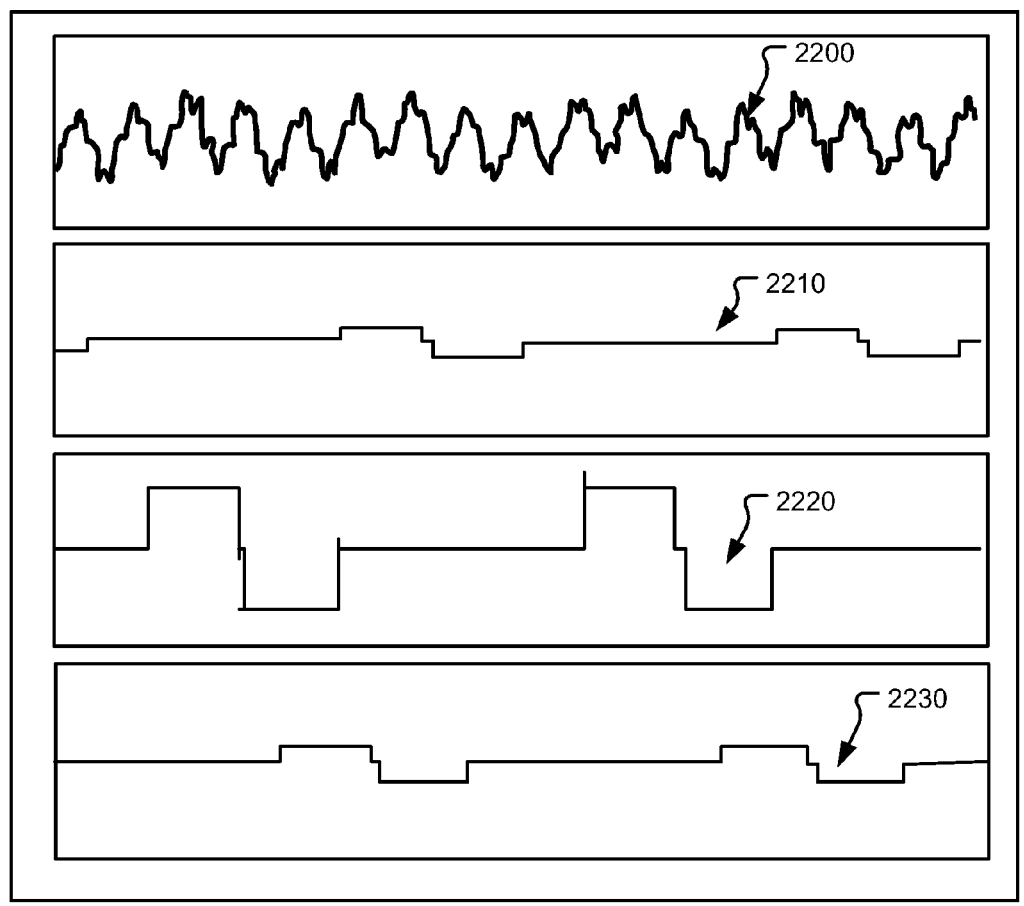
FIGS. 22A and 22B show an output of 3 different channels against the change of sensor #2 input value of 2.5V and 2.8V respectively.
Figure 22B:
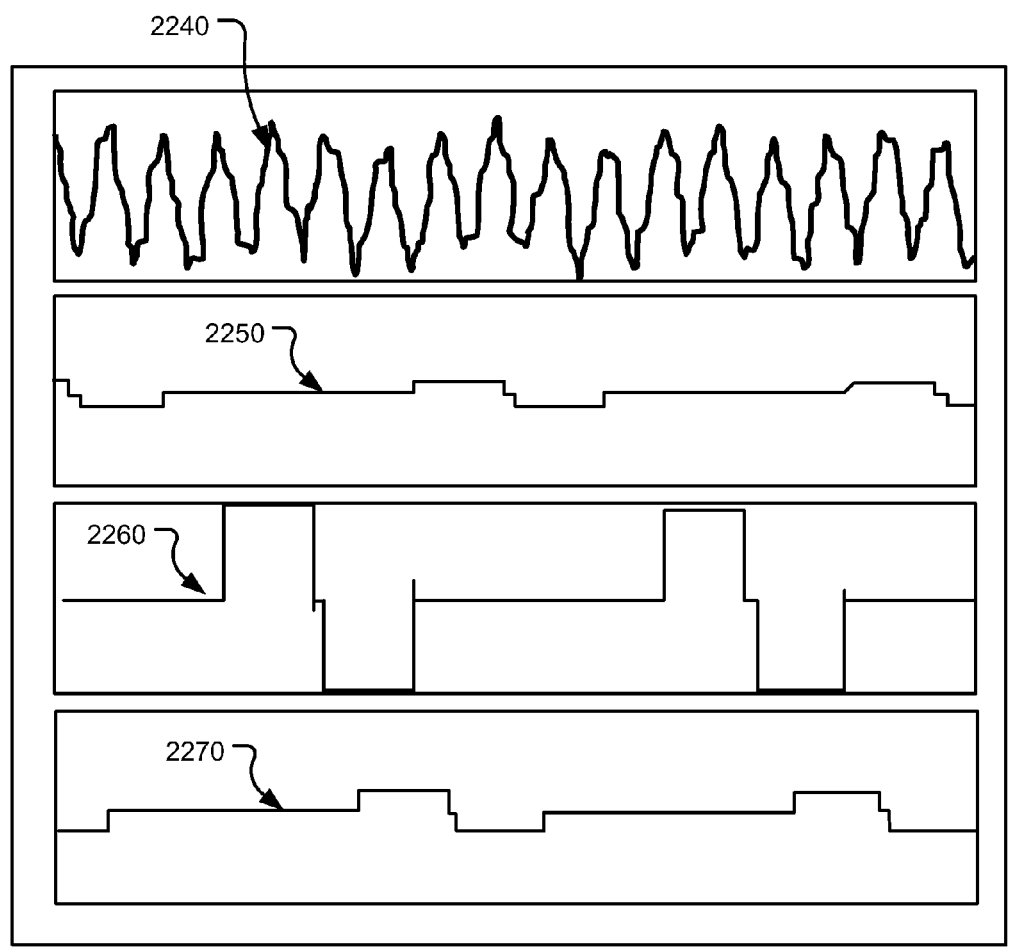

FIGS. 22A and 22B show output signals of different channel (e.g., channels 0, 1 and 2) in response to amplitude change of sensor #2 input value. In FIG. 22A, the output signals 2210, 2220 and 2230 for the different channels are measured after altering the voltage levels of sensor #2 (2200) to 2.5V. In FIG. 22B, the output signals 2250, 2260 and 2270 for the different channels are measured after altering the voltage levels of sensor #2 (2240) to 2.8V.

Figure 23A:
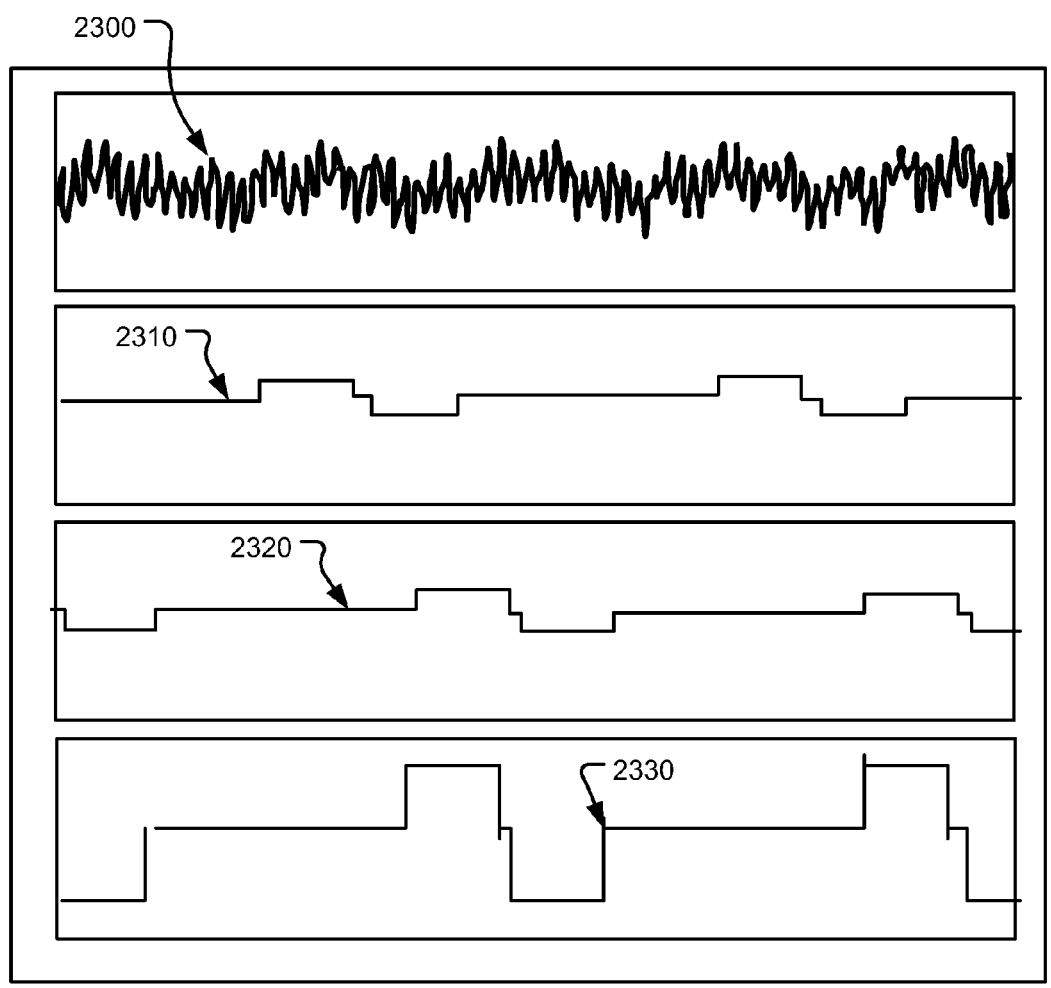
FIGS. 23A and 23B show an output of 3 different channels against the change of sensor #3 input value of 2.5V and 2.8V respectively.
Figure 23B:
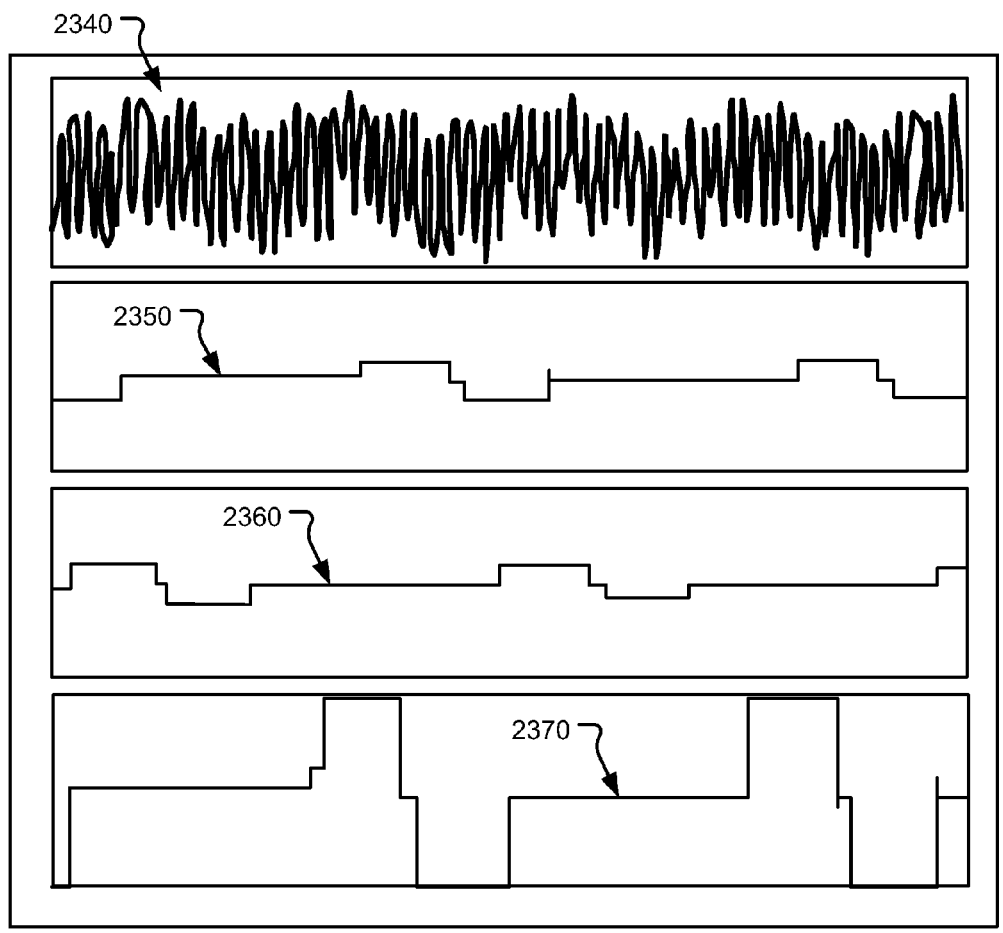

FIGS. 23A and 23B show output signals of different channel (e.g., channels 0, 1 and 2) in response to amplitude change of sensor #3 input value. In FIG. 23A, the output signals 2310, 2320 and 2330 for the different channels are measured after altering the voltage levels of sensor #3 (2300) to 2.5V. In FIG.

22B, the output signals 2350, 2360 and 2370 for the different channels are measured after altering the voltage levels of sensor #3 (2340) to 2.8V.

Figure 24:
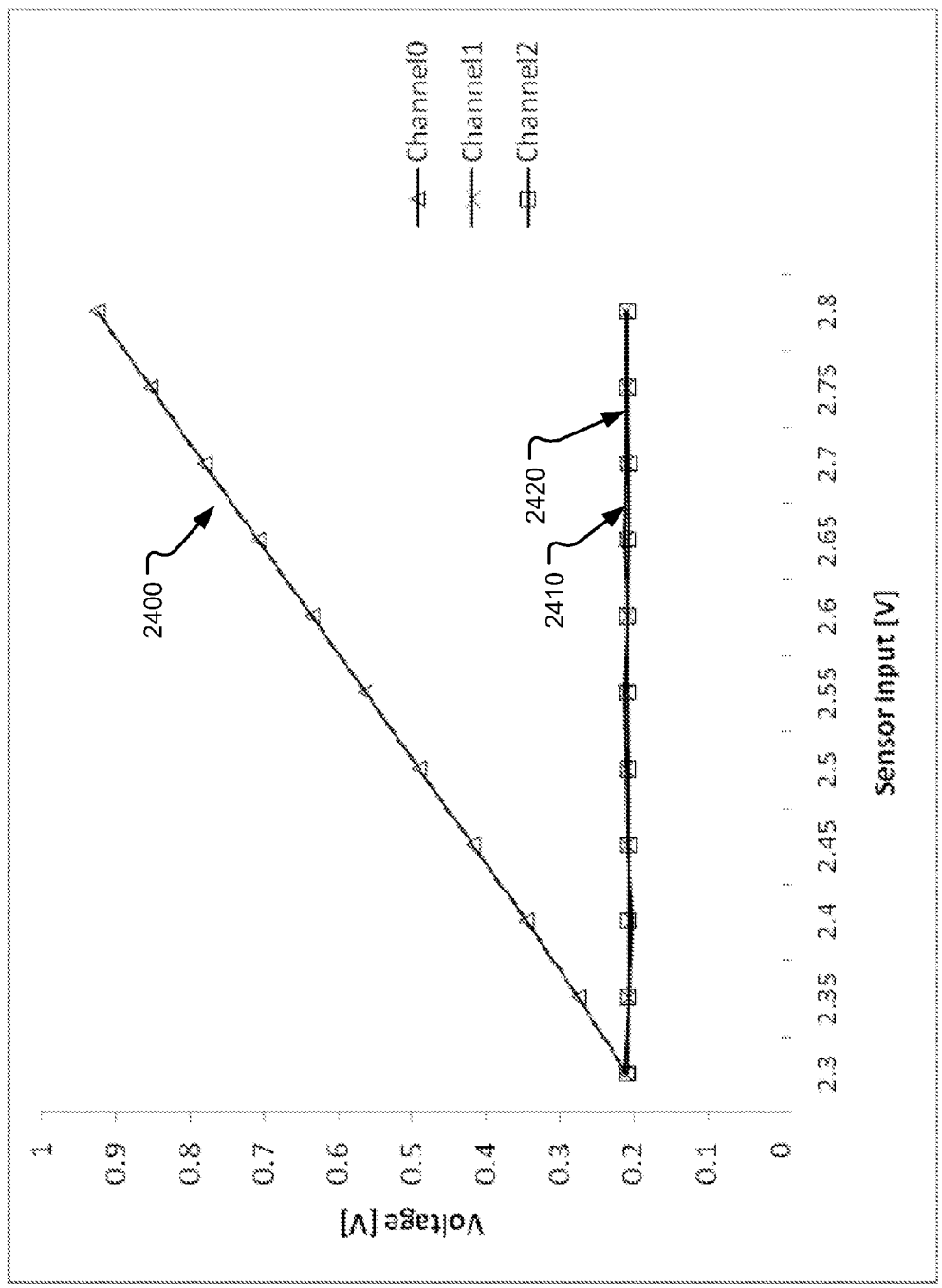
FIG. 24 shows a change of pulse amplitudes from 3 different channels against sensor 1 input value.

FIG. 24 is a data chart that shows a change of pulse amplitudes 2400, 2410 and 2420 from 3 different channels against sensor #1 input value. FIG. 24 shows the characteristics of stimulus pulse amplitude modulation. As shown in FIG. 24, the pulse amplitude 2400 from only a single channel (e.g., channel 0) is modulated by changing a specific sensor input signal (sensor #1). The pulse amplitudes observed from other channels are independent of the first sensor input signal.

Figure 25:
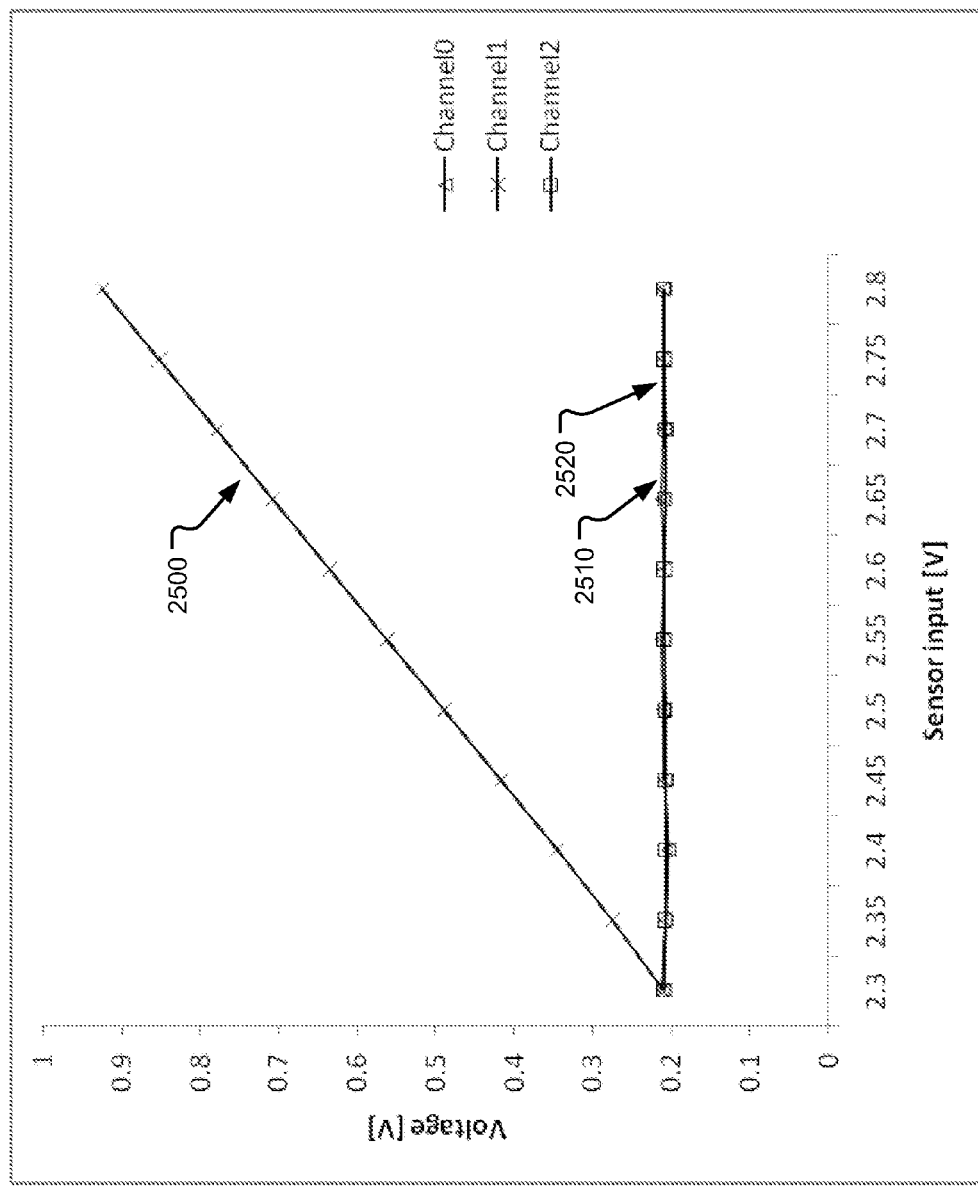
FIG. 25 shows a change of pulse amplitudes from 3 different channels against sensor 2 input value.
Figure 26:
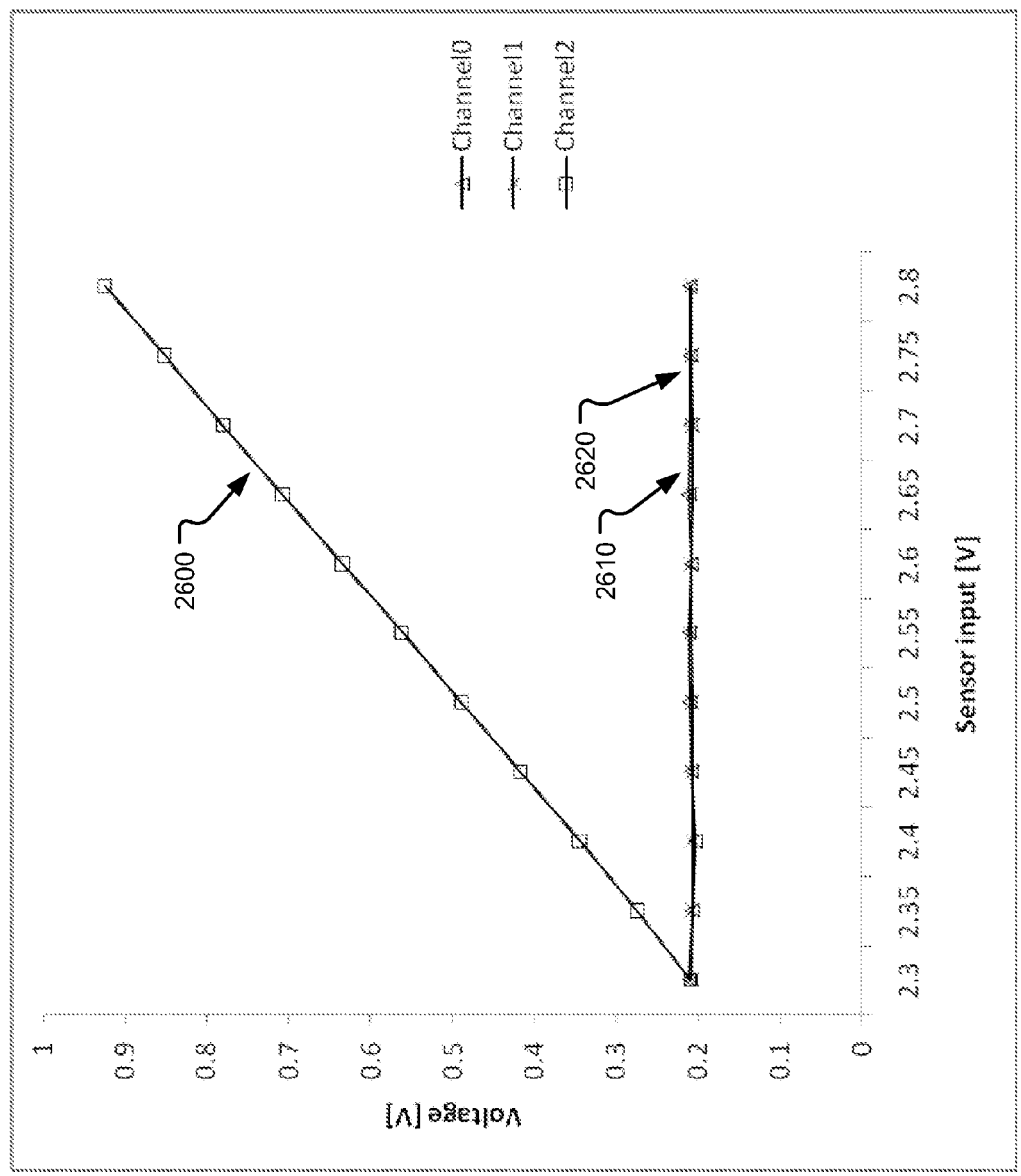
FIG. 26 shows a change of pulse amplitudes from 3 different channels against sensor 3 input value.

FIGS. 25 and 26 also show that different sensor inputs (sensor #2 and #3) can modulate the current amplitudes for specific channels. Specifically, FIG. 25 shows a change of pulse amplitudes from 3 different channels against sensor #2 input value. FIG. 26 shows the change of pulse amplitudes from 3 different channels against sensor #3 input value.

Figure 27A:
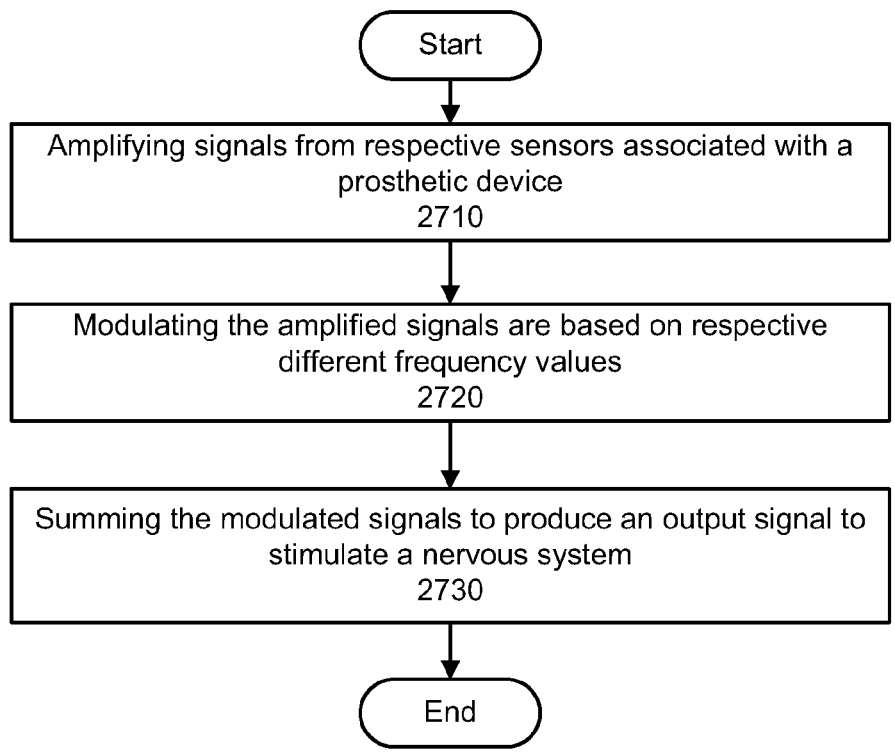
FIGS. 27A, 27B and 27C show process flow diagrams of a process for interfacing with sensors of a prosthesis.
Figure 27B:
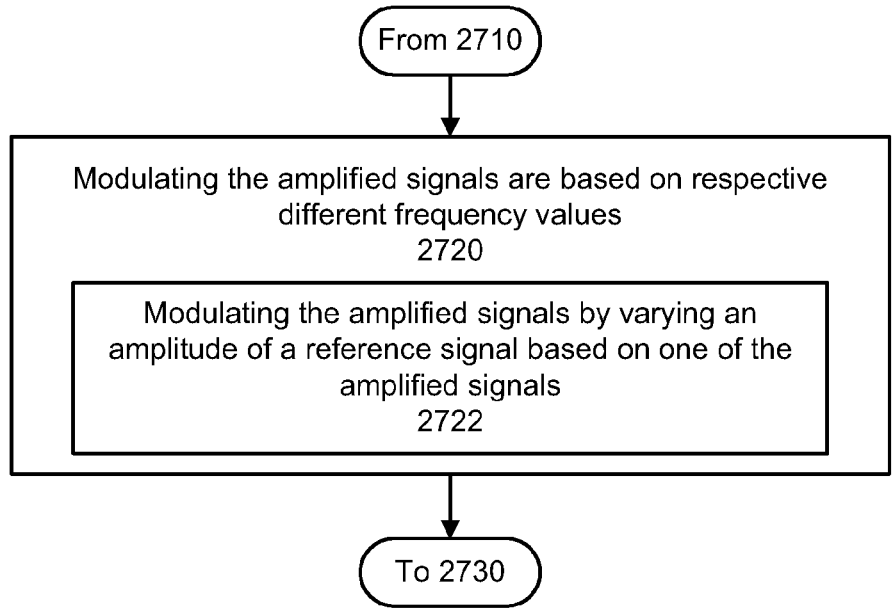
Figure 27C:
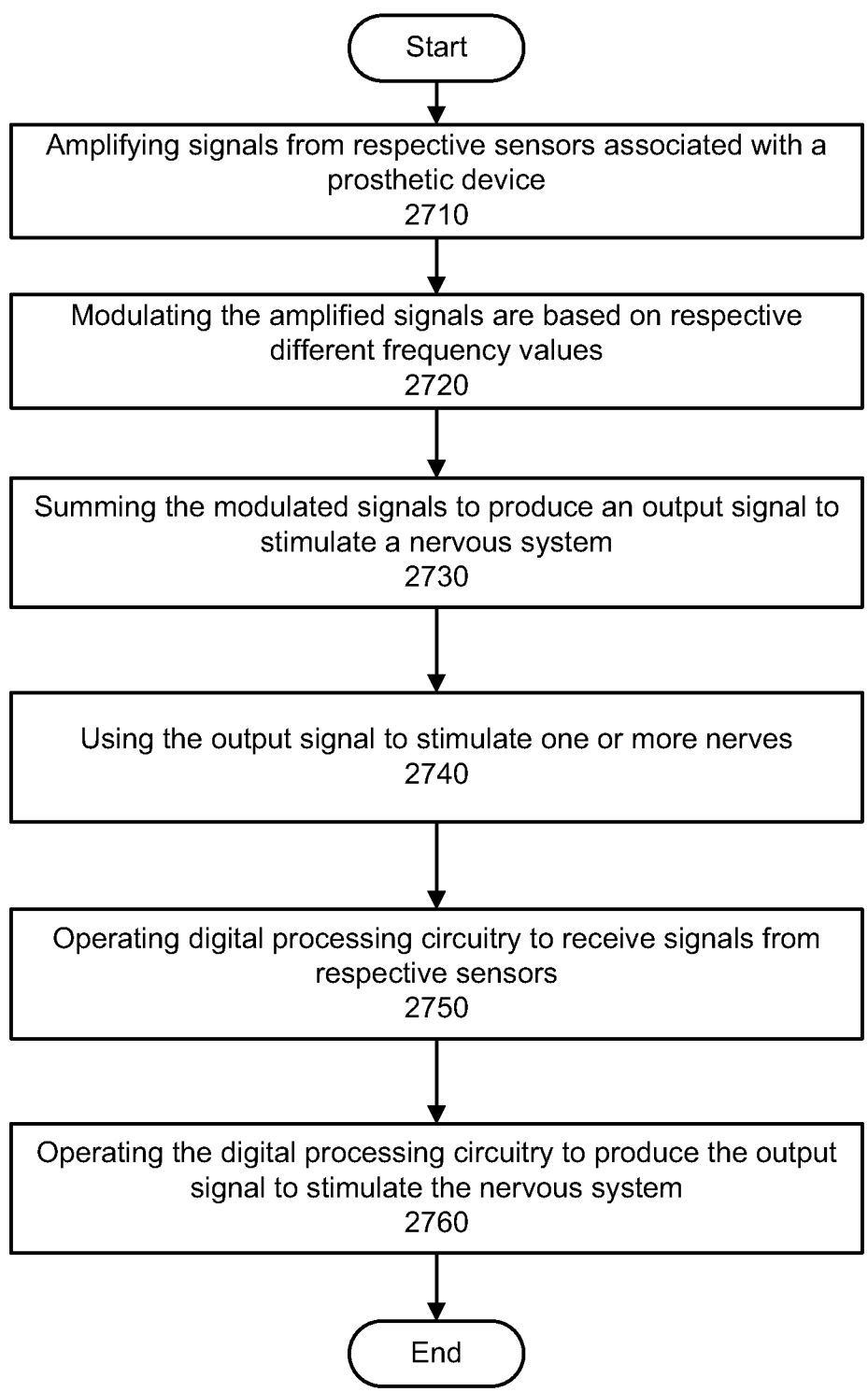

FIGS. 27A, 27B and 27C show process flow diagrams of a process for interfacing with sensors of a prosthesis. For example, a method for interfacing multiple sensors of a prosthetic device includes amplifying signals from respective sensors associated with a prosthetic device (2710). The amplified signals are modulated based on respective different frequency values (2720). Also, the modulated signals are summed to produce an output signal to stimulate a nervous system (2730).

The output signal can be used to stimulate one or more nerves (2740). The amplified signals can be modulated by varying an amplitude of a reference signal based on one of the amplified signals (2722). Also, digital processing circuitry can be operated to receive signals from respective sensors (2750); and the digital processing circuitry can be operated to produce the output signal to stimulate the nervous system (2760).

Implementations of the subject matter and the functional operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special purpose logic circuitry.

While this specification contains many specifics, these should not be construed as limitations on the scope of an invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations are disclosed. However, it is understood that variations and enhancements may be made based on what is described and illustrated in this application including the following claims. For example, different sensors can produce a wide and diverse range of outputs. The inputs from the sensors can be single-ended, or they can be differential. Some sensors can have a wide bandwidth, very low noise, from either high or low impedance sources. High gain may be required for a small sensor voltage. On the other hand, a high gain may cause an amplifier to saturate.

Additionally, a combiner such as a weight summer can sum the outputs of each LPF to produce a signal. Each LPF output can be weighted differently via respective gains of G1, G2, and G3. An output of the combiner can be used to stimulate a nervous system, e.g., providing appropriate, graded, distally referred sensations to the nervous system. The output of the combiner can, for example, control a stimulation of an amputee's nerve stumps with intra-fascicular electrodes and these sensations can be used to provide feedback information such as grip strength and limb position to the amputee. In some implementations, an artificial arm and/or can feature neural control of multiple degrees of freedom, and continuous and simultaneous sensory feedback of limb position and tactile actions. In some implementations, a communication interface circuit can be integrated using complementary metal-oxide-semiconductor (CMOS) technology. Also, the described techniques, apparatus and systems are applicable for any biological tissue in the living system that could be stimulated to provide sensory feedback. For example, the described techniques, apparatus and systems can be used to communicate with vibratory sensors that are being used to provide sensation back via skin stimulation. In addition, the described techniques, apparatus and systems can be applied for augmented sensation in an able-bodied person, (e.g. fighter pilots or teleoperators or surgeons doing non-invasive surgery) rather than being limited to amputees. Additionally, the external device with embedded sensors can include a prosthetic and other external devices. For example, the external device can include devices used by able-bodied persons to perform tasks, such as robotic arms, scissors or probe tips used by surgeons in non-invasive surgery.

What is claimed is:

1. A system comprising:
sensors; and
a communication interface in communication with the sensors, configured to perform operations comprising:
amplifying signals from respective sensors;
modulating the amplified signals based on respective different carrier frequency values such that each amplified signal is placed at a separate carrier frequency from all other amplified signals;
summing the modulated signals to produce a channel signal that can be delivered on a single channel; and
separating signal components of the channel signal and implementing further processing to determine parameters for one or more channels of stimulation of a biological system.

2. The system of claim 1, wherein the communication interface comprises digital processing circuitry to produce the channel signal.

3. The system of claim 1, wherein the communication interface comprises:
amplifiers configured to amplify respective sensor signals;
modulators configured to modulate respective amplified signals, wherein each modulator is configured to use a different frequency for modulation; and
a summer configured to combine outputs of the modulators to produce the channel signal.

4. The system of claim 3, wherein the summer is configured to use a plurality of weight values to control a contribution of respective modulator outputs to the channel signal.

5. The system of claim 3, wherein the communication interface further comprises: an amplifier coupled between one of the modulators and the summer to effect a weighting of the output of the one modulator in the summer.

6. The system of claim 3, wherein at least one of the amplifiers comprises a programmable gain amplifier.

7. The system of claim 3, wherein the communication interface further comprises: low pass filters coupled between respective modulators and the summer.

8. The system of claim 3, wherein each modulator is configured to produce a signal whose amplitude is based on one of the amplified signals.

9. The system of claim 1, further comprising: an external device that comprises the sensors and the communication interface.

10. The system of claim 9, wherein the external device is configured to provide the parameters to the biological system via one or more electrodes.

11. The system of claim 9, wherein the external device comprises a prosthetic device.

12. The system of claim 3, wherein the communication interface further comprises: an amplifier coupled between one of the modulators and the summer to effect a weighting of the output of the one modulator in the summer,
wherein the system further comprises an external device that comprises the sensors and the communication interface,
wherein the external device is configured to provide the parameters to the biological system via one or more electrodes, and
wherein the external device comprises a prosthetic device.

* * * * *